(12) United States Patent
Gill et al.

(10) Patent No.: US 8,946,151 B2
(45) Date of Patent: *Feb. 3, 2015

(54) METHOD OF TREATING PARKINSON'S DISEASE IN HUMANS BY CONVECTION-ENHANCED INFUSION OF GLIAL CELL-LINE DERIVED NEUROTROPHIC FACTOR TO THE PUTAMEN

(75) Inventors: Steven S. Gill, Bristol (GB); Don M. Gash, Lexington, KY (US); Greg A. Gerhardt, Nicholasville, KY (US)

(73) Assignees: Northern Bristol N.H.S. Trust Frenchay Hospital, Bristol (GB); University of Kentucky Research Foundation, Lexington, KY (US); Amgen Inc., Thousand Oaks, CA (US)

( * ) Notice: Subject to any disclaimer, the term of this patent is extended or adjusted under 35 U.S.C. 154(b) by 1083 days.

This patent is subject to a terminal disclaimer.

(21) Appl. No.: 10/963,986

(22) Filed: Oct. 13, 2004

(65) Prior Publication Data

US 2005/0137134 A1 Jun. 23, 2005

Related U.S. Application Data

(63) Continuation-in-part of application No. 10/784,547, filed on Feb. 23, 2004.

(60) Provisional application No. 60/449,789, filed on Feb. 24, 2003.

(51) Int. Cl.
*A61K 38/18* (2006.01)

(52) U.S. Cl.
CPC .................................. *A61K 38/185* (2013.01)
USPC .............................. 514/8.3; 514/8.4; 514/17.7

(58) Field of Classification Search
None
See application file for complete search history.

(56) References Cited

U.S. PATENT DOCUMENTS

| | | |
|---|---|---|
| 3,923,060 A | 12/1975 | Ellinwood |
| 4,003,379 A | 1/1977 | Ellinwood |
| 4,013,074 A | 3/1977 | Siposs |
| 4,146,029 A | 3/1979 | Ellinwood |
| 4,447,224 A | 5/1984 | DeCant |
| 4,588,394 A | 5/1986 | Schulte |
| 4,692,147 A | 9/1987 | Duggan |
| 4,714,462 A | 12/1987 | DiDomenic |
| 4,838,887 A | 6/1989 | Idriss |
| 4,931,050 A | 6/1990 | Idriss |
| 4,978,338 A | 12/1990 | Melsky |
| 5,176,641 A | 1/1993 | Idriss |
| 5,207,666 A | 5/1993 | Idriss |
| 5,575,770 A | 11/1996 | Melsky |
| 5,643,207 A | 7/1997 | Rise |
| 5,720,720 A | 2/1998 | Laske |
| 5,731,284 A | 3/1998 | Williams |
| 5,752,930 A | 5/1998 | Rise |
| 5,908,414 A | 6/1999 | Otto |
| 5,935,795 A * | 8/1999 | Lin et al. .................. 435/7.1 |
| 6,042,549 A | 3/2000 | Amano et al. |
| 6,093,180 A | 7/2000 | Elsberry |
| 6,093,802 A | 7/2000 | Lin |
| 6,184,200 B1 | 2/2001 | Hu |
| 6,309,634 B1 * | 10/2001 | Bankiewicz et al. ........ 424/93.2 |
| 6,319,241 B1 | 11/2001 | King |
| 6,362,319 B1 | 3/2002 | Lin et al. |
| 6,551,290 B1 | 4/2003 | Elsberry |
| 6,589,205 B1 | 7/2003 | Meadows |
| 6,592,571 B1 | 7/2003 | Verbeek et al. |
| 6,609,020 B2 | 8/2003 | Gill |
| 6,620,151 B2 | 9/2003 | Blischak |
| 2001/0027599 A1 | 10/2001 | Elsberrt |
| 2002/0187127 A1 * | 12/2002 | Bankiewicz ................. 424/93.2 |
| 2003/0120262 A1 | 6/2003 | Wieland |
| 2003/0199829 A1 | 10/2003 | Lee |
| 2003/0199831 A1 | 10/2003 | Morris |
| 2003/0208184 A1 | 11/2003 | Burke |
| 2003/0216700 A1 | 11/2003 | Pearson |
| 2003/0216714 A1 | 11/2003 | Gill |
| 2003/0225372 A1 | 12/2003 | Christenson |
| 2005/0119712 A1 | 6/2005 | Shafer |
| 2005/0123526 A1 | 6/2005 | Shafer |

FOREIGN PATENT DOCUMENTS

| | | |
|---|---|---|
| WO | WO 93/06116 | 4/1993 |
| WO | WO 02/07810 | 1/2002 |
| WO | WO 03/002170 | 1/2003 |

(Continued)

OTHER PUBLICATIONS

Mickle et al. Genotype-phenotype relationships in cystic fibrosis. Med Clin North Am. May 2000;84(3):597-607.*
Voet et al. Biochemistry. 1990. John Wiley & Sons, Inc. 126-129 and 228-234.*
Yan et al. Two-amino acid molecular switch in an epithelial morphogen that regulates binding to two distinct receptors. Science 290: 523-527, 2000.*
Yurek. Glial cell line-derived neurotrophic factor improves survival of dopaminergic neurons in transplants of fetal ventral mesencephalic tissue. Exp Neurol. Oct. 1998;153(2):195-202.*

(Continued)

*Primary Examiner* — Gregory S Emch
(74) *Attorney, Agent, or Firm* — Marshall, Gerstein & Borun LLP

(57) ABSTRACT

A method of treating Parkinson's disease in humans is disclosed, wherein glial cell-line derive neurotrophic factor (GDNF) is chronically administered directly to one or both putamen of a human in need of treatment thereof via convection-enhanced infusion using at least one implantable pump and at least one catheter. In one aspect of the present invention the GDNF is infused directly into one or both putamen through one or more indwelling intraparenchymal multiport brain catheters connected to one or more implantable pumps wherein the flow rate is pulsed.

43 Claims, 5 Drawing Sheets

(56) References Cited

FOREIGN PATENT DOCUMENTS

| WO | WO 03/007785 | 1/2003 |
|---|---|---|
| WO | WO 03/077785 | 9/2003 |
| WO | WO 03/090689 A2 | 11/2003 |
| WO | WO 2004/075720 A2 | 9/2004 |
| WO | WO 2005/120548 A1 | 12/2005 |

OTHER PUBLICATIONS

Ai et al., "Intraputamenal infusion of GDNF in aged rhesus monkeys: distribution and dopaminergic effects," *J. Comp. Neurol.* 461:250-261 (2003).
Björklund et al., "Towards a neuroprotective gene therapy for Parkinson's disease: use of adenovirus, AAV and lentivirus vectors for gene transfer of GDNF to the nigrostriatal system in the rat Parkinson model," *Brain Research* 886:82-98 (2000).
Björklund et al., "Parkinson disease gene therapy moves toward the clinic," *Nature Med.* 6:1207-1208 (2000).
Bowenkamp et al., "6-hydroxydopamine induces the loss of the dopaminergic phenotype in substantia nigra neurons of the rat: a possible mechanism for restoration of the nigrostriatal circuit mediated by glial cell line-derived neurotrophic factor," *Exp. Brain Res.* 111:1-7 (1996).
Choi-Lundberg et al., "Dopaminergic neurons protected from degeneration by GDNF gene therapy," *Science* 275:838-841 (1997).
Connor et al., "Differential effects of glial cell line-derived neurotrophic factor (GDNF) in the striatum and substantia nigra of the aged Parkinsonian rat," *Gene Therapy* 6:1936-1951 (1999).
Gash et al., "Functional recovery in parkinsonian monkeys treated with GDNF," *Nature* 380:252-255 (1996).
Gash et al., "Neuroprotective and neurorestorative properties of GDNF," *Ann. Neurol.* 44:S121-S125 (1998).
Grondin et al., "Chronic intracerebral delivery of trophic factors via a programmable pump as a treatment for Parkinsonism," *Methods in Molecular Medicine* 62:257-267 (2001).
Grondin et al., "Chronic, controlled GDNF infusion promotes structural and functional recovery in advanced parkinsonian monkeys," *Brain* 125:2191-2201 (2002).
Grondin et al., "Glial cell line-derived neurotrophic factor increases stimulus-evoked dopamine release and motor speed in aged rhesus monkeys," *J. Neurosci.* 23:1974-1980 (2003).
Hou et al., "Glial cell line-derived neurotrophic factor exerts neurotrophic effects on dopaminergic neurons in vitro and promotes their survival and regrowth after damage by 1-methyl-4-phenylpyridinium," *J. Neurochem.* 66:74-82 (1996).
Kearns et al., "GDNF protects nigral dopamine neurons against 6-hydroxydopamine in vivo," *Brain Research* 672:104-111 (1995).
Kirik et al., "Long-term rAAV-mediated gene transfer of GDNF in the rat Parkinson's model: intrastriatal but not intranigral transduction promotes functional regeneration in the lesioned nigrostriatal system," *J. Neurosci.* 20:4686-4700 (2000).
Kirik et al., Delayed infusion of GDNF promotes recovery of motor function in the partial lesion model of Parkinson's disease, *Eur. J. Neuroscience* 13:1589-1599 (2001).
Kirik et al., "Localized striatal delivery of GDNF as a treatment for Parkinson Disease," *Nature Neuroscience* 7:105-110 (2004).
Kordower et al., "Neurodegeneration prevented by lentiviral vector delivery of GDNF in primate models of Parkinson's disease," *Science* 290:767-773 (2000).
Lindvall et al., "Clinical observations after neural transplantation in Parkinson's disease," *Prog. Brain Res.* 127:299-320 (2000).
Lin et al., "GDNF: a glial cell-line derived neurotrophic factor for midbrain dopaminergic neurons," *Science* 260:1130-1132 (1993).
Lin et al., "Purification and initial characterization of rat B49 glial cell line-derived neurotrophic factor," *J. Neurochem.* 63:758-768 (1994).
Ma et al., "Dyskinesia after fetal cell transplantation for Parkinsonism: a PET study," *Ann. Neurol.* 52:628-634 (2002).

Maswood et al., "Effects of chronic intraputamenal infusion of Glial cell line-derived neurotrophic factor (GDNF) in aged Rhesus monkeys," *Neurobiology of Aging* 23:881-889 (2002).
Olson et al., "Nerve growth factor affects $^{11}$C-nicotine binding, blood flow, EEG, and verbal episodic memory in an Alzheimer patient," *J. Neural Transm.* 4:79-95 (1992).
Olson et al., "Intraputaminal Infusion of nerve growth factor to support adrenal medullary autografts in Parkinson's disease," *Arch. Neurol.* 48:373-381 (1991).
Rosenblad et al., "Intrastriatal glial cell line-derived neurotrophic factor promotes sprouting of spared nigrostriatal dopaminergic afferents and induces recovery of function in a rat model of Parkinson's disease," *Neuroscience* 82:129-137 (1998).
Shults et al., "Intrastriatal injection of GDNF attenuates the effects of 6-hydroxydopamine," *NeuroReport*, 7:627-631 (1996).
Tomac et al., "Protection and repair of the nigrostriatal dopaminergic system by GDNF in vivo," *Nature* 373:335-339 (1995).
Tomac et al., "Retrograde axonal transport of glial cell line-derived neurotrophic factor in the adult nigrostriatal system suggests a trophic role in the adult," *Proc. Natl. Acad. Sci. (USA)*, 92:8274-8278 (1995).
Wenning et al., "Short- and long-term survival and function of unilateral intrastriatal dopaminergic grafts in Parkinson's disease," *Ann. Neurol.* 42: 95-107 (1997).
Zhang et al., "Dose response to intraventricular glial cell line-derived neurotrophic factor administration in Parkinsonian monkeys," *J. Pharmacol. Exp. Ther.* 282:1396-1401 (1997).
International Search Report for International Application No. PCT/US2004/005063 (Sep. 7, 2004).
Gill et al., "Intraparenchymal putaminal administration of glial-derived neurotrophic factor in the treatment of advanced Parkinson's disease," *Neurology* A241:58 (2002).
Brundin, "GDNF treatment in Parkinson's disease: Time for controlled clinical trials?," *Brain* 125:2149-2151 (2002).
Grondin et al., "Glial cell line-derived neurotrophic factor (GDNF): A drug candidate for the treatment of Parkinson's disease," *J. Neurol* 245:P35-P42 (1998).
Ai et al., "Intraputamenal infusion of GDNF in aging rhesus monkeys: Distribution and dopaminergic effects," *J. Comp. Neurol.* 461:250-61 (2003).
Atkinson, "Three standard errors of measurement and the Wechsler memory scale—revised," *Psychological Assessment* 3:136 -138 (1991).
Barbeito et al., "Activation of the bilateral corticostriatal glutamatergic projection by infusion of GABA into thalamic motor nuclei in the cat: An in vivo release study," *Neuroscience* 28:365-374 (1989).
Beck et al., "Mesencephalic dopaminergic neurons protected by GDNF from axotomy-induced degeneration in the adult brain," *Nature* 373:339-341 (1995).
Bobo et al., "Convection-enhanced delivery of macromolecules in the brain," *Proc. Nat. Acad. Sci. U.S.A.* 91:2076-2080 (1994).
Brett et al., "Region of interest analysis using an SPM toolbox," abstract, *NeuroImage* 16 (2002).
Brooks et al., "Differing patterns of striatal $^{18}$F-dopa uptake in Parkinson's disease, multiple system atrophy, and progressive supranuclear palsy," *Ann. Neurol.* 28:547-555 (1990).
Brooks, "The relationship between locomotor disability, autonomic dysfunction, and the integrity of the striatal dopaminergic system in patients with multiple system atrophy, pure autonomic failure, and Parkinson's disease, studied with PET," *Brain*, 113 (Pt 5) 1539-1552 (1990).
Chen et al., "Variables affecting convection-enhanced delivery to the striatum: a systematic examination of rate of infusion, cannula size, Infusate Concentration, and Tissue-Cannula Sealing Time," *J. Neurosurg.* 90:315-20 (1999).
Daniel et al., "Preliminary diagnosis of Parkinson's disease by olfactory bulb pathology," *Lancet* 340:186 (1992).
Defer et al., "Core assessment program for surgical interventional therapies in Parkinson's disease (CAPSIT-PD)," *Mov. Disord.* 14:572-584 (1999).
Freed et al., "Transplantation of embryonic dopamine neurons for severe Parkinson's disease," *N. Engl. J. Med.* 344:710-719 (2001).

(56) References Cited

OTHER PUBLICATIONS

Garnett, "Dopamine visualized in the basal ganglia of living man," *Nature* 305:137-138 (1983).
Gill et al., Direct brain infusion of glial cell line-derived neurotrophic factor in Parkinson disease, *Nat. Med.* 9:589-595 (2003).
Glowinski et al., "Role of the thalamus in the bilateral regulation of dopaminergic and GABAergic neurons in the basal ganglia," *Ciba Found Symp.* Pitman, London, 107:150-163 (1984).
Grondin et al., "Glial cell line-derived neurotrophic factor increases stimulus-evoked dopamine release and motor speed in aged rhesus monkeys," *J. Neurosci.*, 23:1974-1980 (2003).
Hagell, "Dyskinesias following neural transplantation in Parkinson's disease," *Nat. Neurosci.* 5:627-628 (2002).
Hamilton et al., "Heparin coinfusion during convection-enhanced delivery (CED) increases the distribution of the glial-derived neurotrophic factor (GDNF) ligand family in rat striatum and enhances the pharmacological activity of neurturin," *Exp. Neurol.* 168:155-61 (2001).
Hebert et al., "Behavioral and neurochemical effects of intranigral administration of glial cell line-derived neurotrophic factor on aged Fischer 344 rats," *J. Pharm. Exp.* 282:760-768 (1997).
Hebert et al., "Functional effects of GDNF in normal rat striatum: Presynaptic studies using in vivo electrochemistry and microdialysis," *J. Pharm. Exp. Ther.* 279:1181-1190 (1996).
Hoffman et al., "In vivo microdialysis studies on somatodendritic dopamine release in the rat substantia nigra: Effects of unilateral 6-OHDA lesions and GDNF," *Exp. Neurol.* 147:130-141 (1997).
Holm, "A simple sequentially rejective multiple test procedure," *Scand. J. Statist.* 6:65-70 (1979).
Hughes et al., "What features improve the accuracy of clinical diagnosis in Parkinson's disease: A clinicopathologic study," *Neurology* 42:1142-1146 (1992).
Kordower et al., "Clinicopathological findings following intraventricular glial-derived neurotrophic factor treatment in a patient with Parkinson's disease," *Ann Neurol.* 46:419-424 (1999).
Krack et al., "Five-year follow-up of bilateral stimulation of the subthalamic nucleus in advanced Parkinson's disease," *N. Engl. J. Med.* 349:1925-1934 (2003).
Langston et al., "Core assessment program for intracerebral transplantations (CAPIT)," *Mov. Disord.* 7:2-13 (1992).
Lieberman et al., "Convection-enhanced distribution of large molecules in gray matter during interstitial drug infusion," *J. Neurosurg.* 82:1021-1029 (1995).
Martin et al., "Nigrostriatal function in humans studied with positron emission tomography," *Ann. of Neurol.* 26:535-542 (1989).
McCarter et al., "Cognitive functioning after subthalamic nucleotomy for refractory Parkinson's disease," *J. Neurol. Neurosurg. Psychiatry* 69:60-66 (2000).
Miyoshi et al., "Glial cell line-derived neurotrophic factor-levodopa interactions and reduction of side effects in Parkinsonian monkeys," *Ann. Neurol.* 42:208-214 (1997).
Morrish et al., "An [$^{18}$F]dopa-PET and clinical study of the rate of progression in Parkinson's disease," *Brain*: 585-591 (1996).
Morrish et al., "Measuring the rate of progression and estimating the preclinical period of Parkinson's disease with [$^{18}$F]dopa PET," *Neurol., Neurosurg. & Psychiatry* 64:314-319 (1998).
Nguyen et al., "Convective distribution of macromolecules in the primate brain demonstrated using computerized tomography and magnetic resonance imaging," *J. Neurosurg.* 98:584-590 (2003).
Nutt et al., "Randomized, double-blind trial of glial cell line-derived neurotrophic factor (GDNF) in PD," *Neurology* 60:69-73 (2003).
Olanow et al., "A double-blind controlled trial of bilateral fetal nigral transplantation in Parkinson's disease," *Ann. Neurol.* 54:403-414 (2003).
Otsuka et al., "Differences in the reduced $^{18}$F-Dopa uptakes of the caudate and the putamen in Parkinson's disease: Correlations with the three main symptoms," *J. Neurol. Sci.* 136:169-173 (1996).
Pahwa et al., "High-frequency stimulation of the globus pallidus for the treatment of Parkinson's disease," *Neurology* 49:249-253 (1997).
Palfi et al., "Lentivirally delivered glial cell line-derived neurotrophic factor increases the number of striatal dopaminergic neurons in primate models of nigrostriatal degeneration," *J. Neurosci.* 22:4942-4954 (2002).
Pate et al., "Correlation of striatal fluorodopa uptake in the MPTP monkey with dopaminergic indices," *Ann. Neurol.* 34:331-338 (1993).
Patlak et al., "Graphical evaluation of blood-to-brain transfer constants from multiple-time uptake data. Generalizations," *J. Cereb. Blood Flow Metab.* 5:584-590 (1985).
Peto et al., "The development and validation of a short measure of functioning and well being for individuals with Parkinson's disease," *Qual. Life Res.* 4:241-248 (1995).
Quinn et al., "Olfactory threshold in Parkinson's disease," *J. Neurol. Neurosurg. Psychiatry* 50:88-89 (1987).
Rakshi et al., "Frontal, midbrain and striatal dopaminergic function in early and advanced Parkinson's disease A 3D [$^{18}$F]dopa-PET study," *Brain* 122:1637-1650 (1999).
Rascol et al., "Limitations of current Parkinson's disease therapy," *Ann. Neurol.* 53 (Suppl 3):S3-15 (2003).
Romrell et al., "Rationale for current therapies in Parkinson's disease," *Expert Opin. Pharmacother.* 4:1747-1761 (2003).
"The Deep-Brain Stimulation for Parkinson's Disease Study Group," *N. Engl. J. Med.* 345:956-963 (2001).
Wenning et al., "Short- and long-term survival and function of unilateral intrastriatal dopaminergic grafts in Parkinson's disease," *Ann. Neurol.* 42:95-107 (1997).
Whone et al., "The REAL-PET study: Slower progression in early Parkinson's disease treated with ropinirole compared with L-dopa," *Neurology* 58 (Suppl 3): A82-A83 (2002).
International Search Report, PCT/US2005/034347, Apr. 19, 2007.
Bobo et al., "Convention-enhanced delivery of macromolecules in the brain," *Proc. Natl. Acad. Sci. USA* 91:2076-2080 (1994).
Gill et al. "Direct brain infusion of glial cell line-derived neurotrophic factor in parkinson disease," *Nature Medicine* 9:589-595 (2003).
Hamilton et al. "Heparin coinfusion during convection-enhanced delivery (CED) increases the distribution of the glial-derived neurotrophic factor (GDNF) ligand family in rat striatum and enhances the pharmacological activity of neurturin," *Experimental Neurology* 168:155-161 (2001).
Slevin et al. "Improvement of bilateral motor functions in patients with parkinson disease through the unilateral intraputaminal infusion of glial cell line-derived neurotrophic factor," *J. Neurosurg* 102:216-222 (2005).
Amgen press release, "Following Complete Review of Phase 2 Trial Data Amgen Confirms Decision to Halt GDNF Study; Comprehensive Review of Scientific Findings, Patient Safety, Drove Decision," as published on the internet Feb. 11, 2005 at http://www.amgen.com/media/media_pr_detail.jsp?releaseID=673490&year=2005.
Parkinson's Disease Foundation, "Background Information on GDNF—A Timeline," Science News, as published on the internet Sep. 8, 2005 at http://www.pdf.org/news/news.cfm?type=1 &selectedItem=238.

* cited by examiner

P=Putamen
L=Lateral Ventricle

Figure 2(a)-(b)
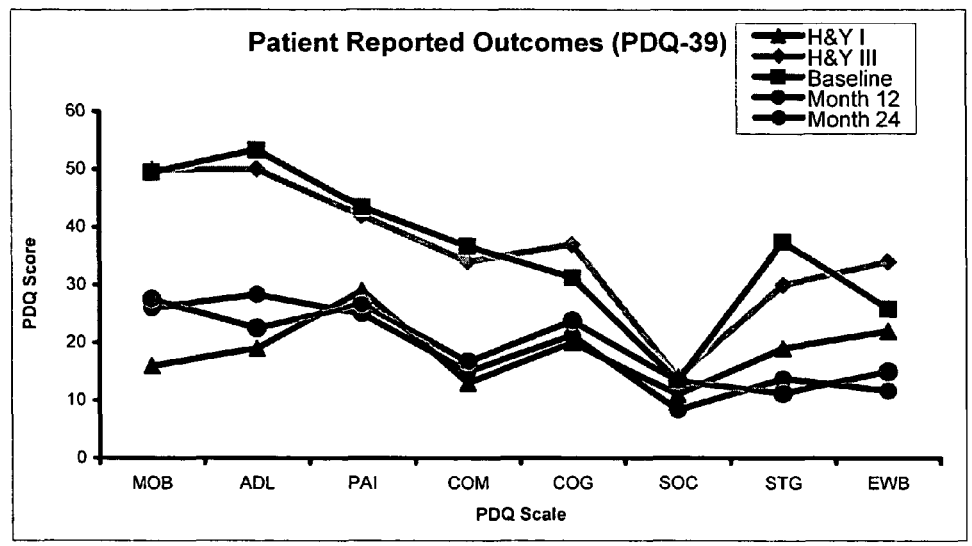
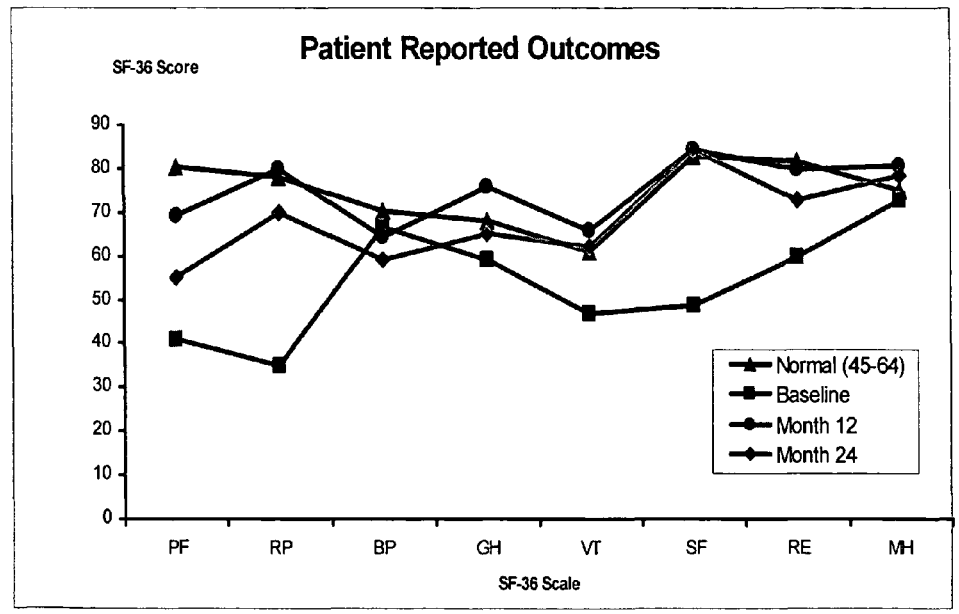

Figure 3(a)
Effects of GDNF on UPDRS and CAPIT clinical rating scores off and on medication

|  |  | Meds | Baseline | Time post GDNF treatment | | |
|---|---|---|---|---|---|---|
|  |  |  |  | 3 Months | 6 Months | 12 Months |
| UPDRS I - | Total | Off | 66 ± 15 | 46 ± 8.9 (-30%) | 44 ± 6.5 (-33%) | 35 ± 11 (-48%) |
|  |  | On | 28 ± 3.7 | 15 ± 3.2 (-48%) | 20 ± 2.4 (-28%) | 15 ± 3.4 (-45%) |
| UPDRS II - of daily living | Activities | Off | 21 ± 3.7 | 15 ± 3.0 (-30%) | 13 ± 2.7 (-37%) | 8.2 ± 3.3 (-61%) |
|  |  | On | 5.2 ± 2.2 | 2.0 ± 1.6 (-62%) | 3.4 ± 0.9 (-35%) | 2.6 ± 2.3 (-50%) |
| UPDRS III - examination | Motor | Off | 33 ± 6.9 | 25 ± 4.8 (-24%) | 23 ± 2.9 (-32%) | 20 ± 7.5 (-39%) |
|  |  | On | 10 ± 2.8 | 6.6 ± 3.6 (-39%) | 9.0 ± 4.1 (-17%) | 6.8 ± 4.2 (-37%) |
| UPDRS IVa - Dyskinesias |  | On | 5.0 ± 2.6 | 1.8 ± 1.1 (-64%) | 3.0 ± 1.5 (-40%) | 1.8 ± 1.1 (-64%) |
| UPDRS IVb - Fluctuations |  | On | 4.8 ± 2.6 | 3.2 ± 1.9 (-33%) | 3.8 ± 1.6 (-21%) | 3.4 ± 1.9 (-29%) |
| CAPIT - supination | Pronation - | Off | 38.4 ± 23 | 16.8 ± 4.9 (-56%) | 16.0 ± 4.0 (-58%) | 14.1 ± 4.4 (-63%) |
|  |  | On | 14.0 ± 3.2 | 11.6 ± 2.1 (-17%) | 11.2 ± 1.9 (-20%) | 10.9 ± 2.3 (-20%) |
| CAPIT - movements | Hand arm | Off | 18.4 ± 5.6 | 10.4 ± 2.9 (-43%) | 9.3 ± 1.9 (-50%) | 8.6 ± 3.2 (-53%) |
|  |  | On | 7.0 ± 1.8 | 5.6 ± 1.0 (-20%) | 5.5 ± 1.1 (-22%) | 5.6 ± 1.5 (-28%) |
| CAPIT - dexterity | Finger | Off | 64.8 ± 45 | 27.7 ± 8.8 (-57%) | 28.2 ± 7.3 (-56%) | 24.5 ± 5.1 (-62%) |
|  |  | On | 27.4 ± 9.4 | 20.9 ± 5.3 (-24%) | 21.6 ± 3.9 (-21%) | 19.8 ± 3.5 (-28%) |
| CAPIT - movements | Leg | Off | 17.1 ± 6.7 | 8.4 ± 1.8 (-51%) | 7.4 ± 2.1 (-56%) | 7.5 ± 1.3 (-56%) |
|  |  | On | 6.6 ± 0.5 | 5.7 ± 0.6 (-14%) | 5.7 ± 0.4 (-14%) | 5.5 ± 0.4 (-17%) |

Figure 3(b)
Effects of GDNF on UPDRS and CAPIT clinical rating scores off and on medication

|  | Meds | Baseline | Time post GDNF treatment | | |
|---|---|---|---|---|---|
|  |  |  | 12 Months | 18 Months | 24 Months |
| UPDRS I - Total | Off | 66 ± 15 | 35 ± 11 (-48%) | 43 ± 17 (-36%) | 28 ± 6.6 (-57%) |
|  | On | 28 ± 3.7 | 15 ± 3.4 (-45%) | 14 ± 3.1 (-51%) | 14 ± 4.5 (-52%) |
| UPDRS II - Activities of daily living | Off | 21 ± 3.7 | 8.2 ± 3.3 (-61%) | 11 ± 5.2 (-46%) | 7.8 ± 1.8 (-63%) |
|  | On | 5.2 ± 2.2 | 2.6 ± 2.3 (-50%) | 2.2 ± 1.1 (-58%) | 2.2 ± 1.3 (-58%) |
| UPDRS III - Motor examination | Off | 33 ± 6.9 | 20 ± 7.5 (-39%) | 26 ± 12 (-24%) | 15 ± 4.3 (-57%) |
|  | On | 10 ± 2.8 | 6.8 ± 4.2 (-37%) | 5.8 ± 2.0 (-46%) | 5.6 ± 3.2 (-48%) |
| UPDRS IVa - Dyskinesias | On | 5.0 ± 2.6 | 1.8 ± 1.1 (-64%) | 1.0 ± 1.2 (-75%) | 1.6 ± 1.1 (-60%) |
| UPDRS IVb - Fluctuations | On | 4.8 ± 2.6 | 3.4 ± 1.9 (-29%) | 3.6 ± 2.1 (-25%) | 3.4 ± 1.7 (-29%) |
| CAPIT - Pronation - supination | Off | 38.4 ± 23 | 14.1 ± 4.4 (-63%) | 14.3 ± 3.2 (-63%) | 13.6 ± 0.7 (-64%) |
|  | On | 14.0 ± 3.2 | 10.9 ± 2.3 (-20%) | 11.1 ± 1.4 (-21%) | 10.6 ± 1.7 (-25%) |
| CAPIT - Hand arm movements | Off | 18.4 ± 5.6 | 8.6 ± 3.2 (-53%) | 10.3 ± 4.0 (-44%) | 7.9 ± 2.9 (-57%) |
|  | On | 7.0 ± 1.8 | 5.6 ± 1.5 (-28%) | 5.1 ± 1.2 (-28%) | 4.8 ± 1.3 (-32%) |
| CAPIT - Finger dexterity | Off | 64.8 ± 45 | 24.5 ± 5.1 (-62%) | 24.9 ± 6.4 (-62%) | 25.2 ± 7.4 (-61%) |
|  | On | 27.4 ± 9.4 | 19.8 ± 3.5 (-28%) | 19.6 ± 3.4 (-28%) | 18.3 ± 4.5 (-33%) |
| CAPIT - Leg movements | Off | 17.1 ± 6.7 | 7.5 ± 1.3 (-56%) | 10.3 ± 4.5 (-40%) | 7.0 ± 0.9 (-59%) |
|  | On | 6.6 ± 0.5 | 5.5 ± 0.4 (-17%) | 5.8 ± 0.3 (-13%) | 5.5 ± 0.4 (-17%) |

UPDRS - Numbers represent average scores for 5 patients ± SD
CAPIT - Numbers represent time (seconds) to complete task ± SD for the left limb

METHOD OF TREATING PARKINSON'S DISEASE IN HUMANS BY CONVECTION-ENHANCED INFUSION OF GLIAL CELL-LINE DERIVED NEUROTROPHIC FACTOR TO THE PUTAMEN

This application is a continuation-in-part of U.S. application Ser. No. 10/784,547 filed Feb. 23, 2004, which claims the benefit of U.S. Provisional Application No. 60/449,789 filed Feb. 24, 2003, which are hereby incorporated by reference in their entirety.

FIELD OF THE INVENTION

The present invention relates generally to the field of neurobiology. More particularly, it concerns methods for treating Parkinson's disease in humans and related methods of restoring atrophic dopaminergic neurons and protecting dopaminergic neurons at risk of degeneration are also described.

BACKGROUND OF THE INVENTION

Current treatments for Parkinson's disease (PD) become increasingly less efficacious as the disease progresses, and do little to slow the underlying pathophysiological changes in the nigrostriatal dopaminergic system (Rascol, O., et al., Limitations of Current Parkinson's Disease Therapy, Ann. Neurol., 53 Suppl 3:S3-12 (2003); Romell, J., et al., Rationale for Current Therapies in Parkinson's Disease, Expert Opin. Pharmacother., 4:1747-1761 (2003)). Neurotrophic factors, proteins which activate cell signaling pathways regulating neuronal survival, differentiation, growth and regeneration, offer promising therapy for treating dopamine neurons in PD, but are difficult to administer clinically as they do not pass through the blood brain barrier (Beck, K. D., et al., Mesencephalic Dopaminergic Neurons Protected by GDNF from Axotomy-Induced Degeneration in the Adult Brain, Nature, 373:339-3416 (1995); Bjorklund, A., et al., Towards a Neuroprotective Gene Therapy for Parkinson's Disease: Use Of Adenovirus, AAV and Lentivirus Vectors for Gene Transfer of GDNF to the Nigrostriatal System in the Rat Parkinson Model, Brain Res., 886:82-98 (2000)). Glial cell line-derived neurotrophic factor (GDNF) is a trophic factor shown to dramatically protect and enhance the function of dopamine neurons in vitro and in vivo in rodents and monkeys (Beck, K. D., et al., (1995); Bjorklund, A., et al., (2000); Gash, D. M., et al., Functional Recovery in Parkinsonian Monkeys Treated with GDNF, Nature, 380:252-255 (1996); Grondin, R., et al., Striatal GDNF Infusion Promotes Structural and Functional Recovery in Advanced Parkinsonian Monkeys. Brain, 125: 2191-2201 (2002); Grondin, R., et al., GDNF Increases Stimulus-evoked Dopamine Release and Motor Speed in Aged Rhesus Monkeys, J. Neurosci., 23:1974-1980 (2003); Hebert M. A., et al., Functional Effects of GDNF in Normal Rat Striatum: Presynaptic Studies Using In Vivo Electrochemistry and Microdialysis. J. Pharm. Exp. Ther., 279:1181-1190 (1996); Hebert M. A. and Gerhardt, G. A., Behavioral and Neurochemical Effects of Intranigral GDNF Administration on Aged Fischer 344 Rats. J. Pharm. Exp. Ther., 282: 760-768 (1997); Hou, J. G. G., et al., Glial Cell line-Derived Neurotrophic Factor Exerts Neurotrophic Effects on Dopaminergic Neurons In Vitro and Promotes Their Survival And Regrowth After Damage by 1-Methyl-4-Phenylpyridinium. J. Neurochem., 66:74-82 (1996); Kordower, J. H., et al., Clinicopathological Findings Following Intraventricular Glial-Derived Neurotrophic Factor Treatment in a Patient with Parkinson's Disease. Ann Neurol., 46(3):419-424 (1999); Kordower, J. H., et al., Neurodegeneration Prevented by Lentiviral Vector Delivery of GDNF in Primate Models of Parkinson's Disease. Science, 290:767-773 (2000); Palfi, S., et al., Lentivirally Delivered Glial Cell Line-derived Neurotrophic Factor Increases the Number of Striatal Dopaminergic Neurons in Primate Models of Nigrostriatal Degeneration. J. Neurosci., 22:4942-4954 (2002); Tomac, A., et al., Protection and Repair of the Nigrostriatal Dopaminergic System by GDNF In Vivo, Nature, 373:335-339 (1995)). However, initial clinical trials involving ventricular delivery of GDNF showed no statistically significant differentiation of the placebo and active treatment groups (Nutt, J. G., et al., ICV GDNF Study Group. Implanted intracerebroventricular. Glial Cell Line-derived Neurotrophic Factor. Randomized, Double-Blind Trial of Glial Cell Line-Derived Neurotrophic Factor (GDNF) in PD, Neurology, 60:69-73 (2003)), perhaps because insufficient amounts of GDNF reached critical target sites from the CSF (Ai, Y., et al., Intraputamenal Infusion in Aging Rhesus Monkeys: Distribution and Dopaminergic Effects. J. Comp Neurol. 461: 250-26125 (2003); Kordower, J. H., et al., (2000)).

Consequently, there continues to exist a long-felt need for effective methods for the treatment and prevention of PD in humans. Accordingly, it is an object of the present invention to provide methods of treating PD in humans comprising intraputaminal convection-enhanced infusion of GDNF. This and other such objectives will be readily apparent to the skilled artisan from this disclosure.

SUMMARY OF THE INVENTION

A first aspect of the present invention concerns a method of treating Parkinson's disease in a human comprising administering a pharmaceutical composition comprising a pharmaceutically effective dose of a glial cell line-derived neurotrophic factor (GDNF) protein product to one or both putamen of a human PD patient in need thereof. The GDNF protein product includes, without limitation, a pharmaceutically effective dose of r-metHuGDNF (a dimeric protein having an the amino acid sequence shown below in Table 1) or variants and/or derivatives thereof. The invention is based on the surprising discovery that convection-enhanced infusion of r-metHuGDNF to one or both putamen of a PD patient by means of at least one implantable pump and one or more indwelling catheters results in dramatic anti-parkinsonian and anti-dyskinetic effects which are further associated with impressive re-innervation and/or restoration of dopamine stores in previously dopamine deficient neurons in human patients afflicted with PD.

The methods of the present invention are contemplated to restore neural cell function in a patient having Parkinson's disease. Furthermore, the methods described herein are useful in repairing neural pathways damaged by Parkinson's disease in humans. Specifically, the methods described herein are capable of stimulating nerve regeneration, including re-innervation of damaged human brain tissue by dopaminergic neurons. In a related aspectthere is provided a method of increasing the function of dopaminergic neurons that comprises convection-enhanced infusion of a pharmaceutically effective dose of r-metHuGDNF to one or both putamen of a human patient in need thereof using at least one implantable pump and at least one catheter.

The present invention also concerns the use of a pharmaceutically effective amount of GDNF and at least one pharmaceutically acceptable vehicle, excipient, or diluent in the preparation of a pharmaceutical composition for increasing the function of dopaminergic neurons, wherein the composition is administered to one or both putamen of a human in need thereof via convection-enhanced infusion using at least one implantable pump and at least one catheter.

Additionally provided are methods of treating cognitive disorders in humans that comprise administration of a pharmaceutically effective dose of r-metHuGDNF to one or both putamen of a human patient in need thereof via convection-enhanced infusion using at least one implantable pump and at least one catheter.

Another aspect of the present invention includes methods of treating PD or cognitive disorders comprising the administration of a pharmaceutically effective dose of r-metHuGDNF to one or both putamen of a human in need thereof via convection-enhanced infusion using at least one implantable pump and at least one catheter and assessing dopaminergic function in the brain of said human pre-operatively, and, optionally, assessing dopaminergic function in the brain of said human periodically post-operatively.

The methods disclosed herein may also provide a prophylactic function in humans. More specifically, one embodiment of the present invention includes a method of preventing PD in a human comprising administration of r-metHuGDNF to one or both putamen of a human via convection-enhanced infusion using at least one implantable pump and at least one catheter. Another embodiment of the present invention includes methods of preserving dopaminergic neural cell function in a human having, or at risk of having, a neurodegenerative disorder comprising administration of r-metHuGDNF to one or both putamen of a human via convection-enhanced infusion using at least one implantable pump and at least one catheter. The neurodegenerative disorder may be Parkinson's disease or multiple system atrophy (MSA). According to the invention, r-metHuGDNF administered via convection-enhanced infusion to the human putamen is contemplated to preserve the integrity of the nigrostriatal pathway in the human brain. Prophylactically administering GDNF via convection-enhanced infusion of r-metHuGDNF in accordance with the invention is contemplated as a method of preventing or treating degeneration of the nigrostriatal pathway or loss of functional dopaminergic activity associated with a neurodegenerative disorder. The neurodegenerative disorder prevented or treated includes Parkinson's disease and MSA.

BRIEF DESCRIPTION OF THE DRAWINGS

FIGS. 2(a) and 2(b) depicts patient assessments made using validated quality of life questionnaires: the 39-item Parkinson's Disease Questionnaire (PDQ 39; FIG. 2(a)) and the 36-item Medical Outcomes Study short form health survey (SF-36; FIG. 2(b)) before surgery and after 3, 6, 12, 18, and 24 months of convection-enhanced infusion of r-metHuGDNF to the putamen, either unilaterally or bilaterally, using one or more single-port catheters.

FIGS. 3(a) and 3(b) depicts the UPDRS scores for patients at 0, 3, 6, 12, 18, and 24 months of convection-enhanced infusion of r-metHuGDNF to the putamen, either unilaterally or bilaterally using one or more single-port catheters.

DETAILED DESCRIPTION OF CERTAIN PREFERRED EMBODIMENTS

Figure 1A:
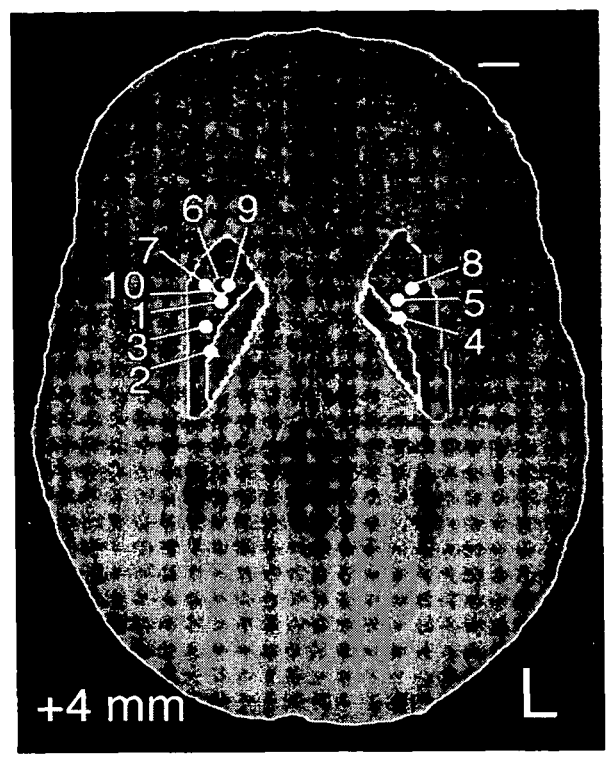
FIGS. 1(a) and 1(b) illustrate the placement of multiport infusion catheters (represented by white circles except patient 6, represented by a black circle for clarity). Images were normalized to the Talirach atlas in Analyze version 5.0, and the catheter locations mapped to a single axial slice level (+4 mm). The target for multiport catheter placement was the mid-dorsal putamen. Numbers indexing each location represent the corresponding patient designation. The reference anatomic underlay is the Talairach-normalized average T1-weighted image with superimposed lenticular nucleus map (dark grey—putamen; light grey—globus pallidus) from the ten subjects. L—Patient Left. Scale Bar (top right)—10 mm.

This invention is based on the discovery that convection-enhanced infusion of GDNF to one or both putamen of a human PD patient using at least one implantable pump and at least one indwelling catheter results in surprisingly dramatic anti-parkinsonian and anti-dyskinetic effects which are associated with impressive re-innervation and restoration of dopamine stores in previously dopamine deficient neurons.

Macromolecules like GDNF diffuse slowly in brain parenchyma and usually over only short distances (Bobo, R. H., et al., Convection-Enhanced Delivery of Macromolecules in the Brain. Proc. Nat. Acad. Sci U.S.A., 91:2076-2080 (1994)). Convection enhanced delivery (CED) to the brain uses bulk flow in the extracellular space that results from a pressure gradient to significantly enhance tissue penetration and distribute macromolecules over larger volumes in relatively homogenous concentrations and largely independent of molecular weight. This is in stark contrast to diffusion that is dependent on establishing a concentration gradient and depends heavily on molecular weight (Bobo, et al., (1994); U.S. Pat. Nos. 5,720,720, 6,093,802 and 6,184,200 (the U.S. patents are hereby incorporated by reference in their entirety); Chen, M. Y., et al., Variables Affecting Convection-Enhanced Delivery to the Striatum: a Systematic Examination of Rate of Infusion, Cannula Size, Infusate Concentration, and Tissue-Cannula Sealing Time, J. Neurosurg., 90:315-20 (1999); Hamilton, J. F., et al., Heparin Coinfusion During Convection-Enhanced Delivery (CED) Increases the Distribution of the Glial-Derived Neurotrophic Factor (GDNF) Ligand Family in Rat Striatum and Enhances the Pharmacological Activity of Neurturin, Exp. Neurol., 168: 155-61 (2001); Nguyen, T. T., et al., Convective Distribution of Macromolecules in the Primate Brain Demonstrated Using Computerized Tomography and Magnetic Resonance Imaging, J. Neurosurg., 98:584-90 (2003)). In a recent study in nonhuman primates (Gash, et al., unpublished data), GDNF was seen to have an average area of distribution of $31\pm8$ mm$^2$ when delivered with a single port catheter (1 mm in diameter with a 0.25 mm diameter port at the tip; Medtronic model 8770IP1A) and $119\pm16$ mm$^2$ with a multiport catheter (1 mm in diameter with 24 ports, each 0.075 mm in diameter; Medtronic model 8770IP24A) using the same pump delivery parameters. This finding is consistent with other studies that show convection-enhanced infusion distributes large molecules far more extensively at a relatively homogenous concentration as compared to diffusion alone (Lieberman, D. M., et al., Convection-Enhanced Distribution of Large Molecules in Gray Matter During Interstitial Drug Infusion, J. Neurosurg., 82:1021-1029 (1995)).

One aspect of the present invention provides methods of treating or preventing neurodegenerative disorders in a human that comprise administering a pharmaceutical composition comprising a pharmaceutically effective amount of a GDNF protein product and at least one pharmaceutically acceptable vehicle, excipient, or diluent to one or both putamen of a human in need thereof via convection-enhanced infusion using at least one implantable pump and at least one catheter. The neurodegenerative disorder may be Parkinson's disease or MSA.

In another embodiment of the present invention, in conjunction with the above and below embodiments, at least one catheter is a multiport catheter. Additionally (or alternatively), the infusion may be pulsed.

In another embodiment of the present invention, in conjunction with the above and below embodiments, at least one catheter may be a single-port catheter from about 1 mm in diameter to about 0.5 mm in diameter and wherein the port is at its distal end. Additionally (or alternatively), the infusion may be pulsed.

Another embodiment of the present invention provides a method of treating Parkinson's disease in a human that comprises administering a pharmaceutical composition comprising a pharmaceutically effective amount of a GDNF protein product and at least one pharmaceutically acceptable vehicle, excipient, or diluent to one or both putamen of a human in need thereof via convection-enhanced infusion of the pharmaceutical composition using at least one implantable pump and at least one catheter with a single port at its distal end. Another embodiment of the present invention provides a method of treating Parkinson's disease in a human that comprises administering a pharmaceutical composition comprising a pharmaceutically effective amount of a GDNF protein product and at least one pharmaceutically acceptable vehicle, excipient, or diluent to one or both putamen of a human in need thereof via convection-enhanced infusion of the pharmaceutical composition using at least one implantable pump and at least one catheter with a single port at its distal end and wherein the infusion of the composition is pulsed.

The methods of the present invention may comprise continuous and/or pulsed delivery of GDNF through one or more catheters with a diameter of about 1 mm to about 0.5 mm and having a single port at its distal end to promote convection enhanced distribution of GDNF which allows local tissue concentrations of GDNF to reach threshold levels. In some embodiments of the invention, the method comprises continuous and/or pulsed delivery of GDNF utilizing one or more catheters with a diameter of about 0.8 mm to about 0.6 mm and having a single port at its distal end to promote convection enhanced distribution of GDNF which allows local tissue concentrations of GDNF to reach threshold levels. In other embodiments of the invention, the method comprises continuous and/or pulsed delivery of GDNF utilizing one or more catheters with a diameter of about 0.6 mm and having a single port at its distal end to promote convection enhanced distribution of GDNF which allows local tissue concentrations of GDNF to reach threshold levels.

Unilateral delivery of GDNF by a pulsed flow sequence administered contralaterally to the most affected side using a multi-port catheter resulted in motor improvement bilaterally comparable to improvement seen for bilateral putamenal GDNF continuous using a 0.6 mm diameter single port catheter (Gill, et al., (2003)). With both approaches, the total UPDRS scores improved in OFF and ON after 6 months of GDNF treatment. Timed motor tests also improved, with improvements seen in both ON and OFF. Patients administered GDNF contralaterally to the most affected side, did not experience aphthous mouth ulcers and only two reported mild Lhermitte's syndrome. Bilateral effects were observed in all ten subjects. These bilateral improvements associated with unilateral GDNF treatment as disclosed herein support a facilitatory effect of improved function in the ipsilateral putamen on bilateral motor pathways. Furthermore, the apparent bilateral effects from unilateral administration of GDNF are surprising and unexpected in that they are not consistent with the known dopaminergic circuitry of the basal ganglia, but are consistent with crossed glutamatergic projections from the motor cortex (Barbeito, L., et al., Activation of the Bilateral Corticostriatal Glutamatergic Projection by Infusion of GABA into Thalamic Motor Nuclei in the Cat: an In Vivo Release Study, Neuroscience, 28:365-374 (1989); Glowinski, J., et al., Role of the Thalamus in the Bilateral Regulation of Dopaminergic and GABAergic Neurons in the Basal Ganglia. Ciba Found Symp. 107:150-163 (1984)).

Accordingly, effective methods of treating or preventing the pathological hallmarks of Parkinson's disease in humans as well as the devastating symptoms of PD are provided by the present invention.

The section headings used herein are for organizational purposes only and are not to be construed as limiting the subject matter described.

Abbreviations

In the preceding description and the experimental disclosure which follows, the following abbreviations apply:

| | |
|---|---|
| 6-OHDA | 6-hydroxydopamine |
| ALS | amyotrophic lateral sclerosis |
| ASA | acute systemic anaphylaxis |
| AUC | area under the concentration vs time curve |
| CAPIT | Core Assessment Program for Intracerebral Transplantations |
| CAPS | 3-(cyclohexylamino)-1-propanesulfonic acid |
| CHO | Chinese hamster ovary |
| CI | continuous infusion |
| CSF | cerebrospinal fluid |
| CT | computed tomography |
| DA | dopamine, dopaminergic |
| DOPAC | 3,4-dihydroxyphenylacetic acid |
| E. coli | Escherichia coli |
| FCA | Freund's Complete Adjuvant |
| GDNF | glial cell line-derived neurotrophic factor |
| GLP | Good Laboratory Practice |
| HPLC | high-performance liquid chromatography |
| HVA | homovanillic acid |
| ICV | intracerebroventricular |
| IM | intramuscular |
| ISN | intranigral |
| IT | intrathecal |
| IV | intravenous |
| L-dopa | 3,4-dihydroxyphenylalanine (levodopa) |
| r-metHuGDNF | recombinant-methionyl human GDNF |
| MPTP | 1-methyl-4-phenyl-1,2,3,6-tetrahydropyridine |
| PD | Parkinson's disease |
| PET | positron-emission tomography |
| pmn | progressive motor neuropathy |
| Ret | receptor tyrosine kinase |
| r-metHuGDNF | recombinant-methionyl human GDNF |
| SC | subcutaneous |
| SDS-PAGE | sodium dodecylsulfate-polyacrylamide gel electrophoresis |
| SEM | standard error of the mean |
| TGF | transforming growth factor |
| TH | tyrosine hydroxylase |
| TH+ | tyrosine hydroxylase positive |
| UPDRS | Unified Parkinson's Disease Rating Scale |

DEFINITIONS

Unless otherwise noted, technical terms are used according to conventional usage. As utilized in accordance with the present disclosure, the following terms shall be understood to have the following meanings:

As used herein, the term "catheter" refers to any tubular medical device for insertion into a cavity, tissue, organ, or any substructure thereof of a living mammal to permit injection of a therapeutic agent. As particularly used here, a catheter is used to deliver r-metHuGDNF to the brain or substructures thereof such as the putamen. An "indwelling" catheter is one that is implanted and left in place for protracted periods, such as fifteen minutes or longer.

As used herein, the phrase "catheter system" refers to the combination of at least one catheter and at least one accessory device including, but not limited to, an anchor, stylet, guide tube, guide wire or a combination thereof.

"Continuous delivery" or "chronic infusion" are interchangeable and are intended to mean delivery of a substance over a period of time such that the procedure is distinguished from "bolus" delivery. Continuous delivery generally involves the delivery of a substance over a period of time without interruption. The rate of delivery need not be constant, and may be pulsed, and the period of delivery need not be very long, i.e., the period of constant delivery may be over a period of maybe half an hour or an hour or a few hours, but may also be over a period of days, weeks, months, or even years. A pulse consists of periodic increases in the flow rate for intervals ranging from seconds to minutes, to hours, which, as used herein, enhances convection enhanced delivery of the drug into brain tissue.

"Admixing" as used herein denotes the addition of an excipient to a polypeptide of interest, such as by mixing of dry reagents or mixing of a dry reagent with a reagent in solution or suspension, or mixing of aqueous formulations of reagents.

"Excipient" as used herein denotes a non-therapeutic agent added to a pharmaceutical composition to provide a desired consistency or stabilizing effect.

"Implanted" means placed within the body, and maintained at that location for some extended period of time. As used herein it is intended that the period of time during which the implanted object is maintained in place will be, in general, considerably greater than that customarily required to introduce a bolus of a substance, such as a drug. For example, a catheter used in a method of the invention may be placed within a tissue or organ such that the catheter so implanted is intended to remain at the site of implantation for some extended period of time. Some of the drug delivery apparatuses that may be used in the methods of the invention, for example the drug pumps and/or catheters, are designed to be implanted for periods greater than a month and even years and to deliver drug during this period. A drug delivery apparatus may be implanted, for example, subcutaneously, or within a tissue or organ, or within a body cavity such as the peritoneal cavity, infraclavicular space, the thoracic cavity, the pelvic cavity, or any other cavity or location that is convenient for delivery of the intended substance. A catheter may be implanted into a tissue, for example into brain tissue, and may be affixed in place by fixing the catheter to another tissue, such as bone, e.g., the skull, or cartilage, using an adhesive or screws, clamps, sutures or any other suitable fixing means.

The phrases "dopaminergic dysfunction", "dopaminergic dysregulation", "dopaminergic degeneration", "dopamine depleted", "dopamine deficient", or grammatical equivalents thereof, may be used interchangeably herein. All such phrases are intended to encompass at least one of the following conditions or disorders: Parkinson's disease, neuronal dopamine deficit, dopaminergic neuron deficit, dopaminergic neuron lesions, hypo-dopaminergic innervation, dopamine synthesis incapacity, dopamine storage incapacity, dopamine transport incapacity, or dopamine uptake incapacity. Dopaminergic dysfunction can be evidenced by analyzing factors including, but not limited to, the following: 1) the number of TH expressing neurons 2) size of dopamine neuronal cells 3) dopamine metabolite levels 4) dopamine uptake, 5) dopamine transport, 6) neuronal dopamine uptake, 7) dopamine transporter binding, 8) quantal size of terminal dopamine release, 9) rate of dopamine turnover, 10) TH+ cell count, 11) TH+ innervation density and 12) TH+ fiber density.

The phrase "target site", or a grammatical version thereof, refers to the site for intended delivery of a substance, such as a drug. In particular embodiments of the present invention, a preferred target site is an area of dopaminergic degeneration or dopaminergic dysfunction within the brain of a human afflicted with Parkinson's disease. More preferably, the target site includes one or more site in the substantia nigra, globus pallidus, caudate nucleus, and putamen. Even more preferably, the target site includes the central area of the putamen. Even more preferably, the target site includes the posterior area of the putamen. Most preferably, the target site includes the postero-dorsal area of the putamen. Furthermore, a particular target site may be targeted unilaterally or bilaterally with respect to the hemispheres of the brain.

"Proximal end" is a relative term, and generally refers to the end of a device, such as a catheter that is nearest to the operator (i.e., the surgeon) and is furthest away from the treatment site. In the present invention a catheter has a proximal end that may be communicably attached to an access port or drug delivery apparatus, such as a pump, or reservoir.

"Tyrosine hydroxylase-positive" or "TH+" is intended to refer to the presence of tyrosine hydroxylase in a referenced nervous tissue as indicated by the results from any technique known in the art as a means to detect and/or measure tyrosine hydroxylase, tyrosine hydroxylase encoding mRNA, or tyrosine hydroxylase activity.

"Distal end" is a relative term and generally refers to the end of a device, such as a catheter, that is furthest away from the operator (i.e., the surgeon) and is closest to the treatment site. In the present invention the distal end of a catheter may be communicably attached to an opening that allows for the delivery of drug to the target site.

"Drug delivery apparatus" as used herein includes but is not limited to, a drug reservoir and/or a drug pump of any kind, for example an osmotic pump, an electromechanical pump, an electroosmotic pump, an effervescent pump, a hydraulic pump, a piezoelectric pump, an elastomeric pump, a vapor pressure pump, or an electrolytic pump. Preferably, such a pump is implanted within the body.

Throughout this specification, reference to the term "GDNF" or the phrase "GDNF protein product" or "GDNF polypeptide", all of which are used interchangeably, refers to glial cell line-derived neurotrophic factor from any species, including murine, bovine, ovine, porcine, equine, avian, and preferably human, in native sequence or in genetically engineered variant form, including, without limitation, biologically active fragments, analogs, variants, (including, insertion, substitution, and deletion variants) and derivatives thereof, and from any source, whether natural, synthetic, or recombinantly produced.

Exemplary GDNF polypeptides useful in the present invention include, without limitation, any of GDNF protein products described in U.S. Pat. Nos. 5,731,284, 6,362,319, 6,093,802, and 6,184,200 (all of which are hereby incorporated by reference in their entireties). Preferred GDNF protein products for use in the methods of the present invention include, but are not limited to, r-metHuGDNF, a recombinant GDNF protein produced in E. coli which has an amino acid sequence identical to native mature human GDNF with the addition of an amino terminal methionine. Thus, r-metHuGDNF consists of 135 amino acids. Seven of the amino acids are cysteines, which are involved in one intermolecular disulfide bond and three intramolecular disulfide bonds. In its active form, r-metHuGDNF is a disulfide-bonded homodimer. The primary amino acid sequence of monomeric r-metHuGDNF (SEQ ID NO: 1) is provided in Table 1.

TABLE 1

Primary Amino Acid Sequence of r-metHuGDNF

| Primary Amino Acid Sequence | | | | | | | | | | Amino Acid No. |
|---|---|---|---|---|---|---|---|---|---|---|
| H$_2$N-Met | Ser | Pro | Asp | Lys | Gln | Met | Ala | Val | Leu | Pro | 10 |
| | Arg | Arg | Glu | Arg | Asn | Arg | Gln | Ala | Ala | Ala | 20 |
| | Ala | Asn | Pro | Glu | Asn | Ser | Arg | Gly | Lys | Gly | 30 |
| | Arg | Arg | Gly | Gln | Arg | Gly | Lys | Asn | Arg | Gly | 40 |
| | Cys | Val | Leu | Thr | Ala | Ile | His | Leu | Asn | Val | 50 |
| | Thr | Asp | Leu | Gly | Leu | Gly | Tyr | Glu | Thr | Lys | 60 |
| | Glu | Glu | Leu | Ile | Phe | Arg | Tyr | Cys | Ser | Gly | 70 |
| | Ser | Cys | Asp | Ala | Ala | Glu | Thr | Thr | Tyr | Asp | 80 |
| | Lys | Ile | Leu | Lys | Asn | Leu | Ser | Arg | Asn | Arg | 90 |
| | Arg | Leu | Val | Ser | Asp | Lys | Val | Gly | Gln | Ala | 100 |
| | Cys | Cys | Arg | Pro | Ile | Ala | Phe | Asp | Asp | Asp | 110 |
| | Leu | Ser | Phe | Leu | Asp | Asp | Asn | Leu | Val | Tyr | 120 |
| | His | Ile | Leu | Arg | Lys | His | Ser | Ala | Lys | Arg | 130 |
| | Cys | Gly | Cys | Ile | COOH | | | | | | 134 |

The GDNF protein products useful in the present invention may be isolated or generated by any means known to those skilled in the art. Preferably, GDNF is recombinantly produced. In a preferred method, the GDNF is cloned and its DNA expressed, e.g., in mammalian cells or bacterial cells. Exemplary methods for producing GDNF protein products useful in the present invention are described in U.S. Pat. Nos. 6,362,319, 6,093,802 and 6,184,200 (all of which are hereby incorporated by reference in their entireties).

GDNF pharmaceutical compositions typically comprise a therapeutically effective amount of at least one GDNF protein product and one or more pharmaceutically and physiologically acceptable formulation agents. Suitable formulation agents include, but are not limited to, antioxidants, preservatives, coloring, flavoring and diluting agents, emulsifying agents, suspending agents, solvents, fillers, bulking agents, buffers, vehicles, diluents, excipients and/or pharmaceutical adjuvants. For example, a suitable vehicle may be, physiological saline solution, citrate buffered saline, or artificial CSF, possibly supplemented with other materials common in compositions for parenteral administration. Neutral buffered saline or saline mixed with serum albumin are further exemplary vehicles. Those skilled in the art would readily recognize a variety of buffers that could be used in the compositions, and dosage forms used in the invention. Typical buffers include, but are not limited to pharmaceutically acceptable weak acids, weak bases, or mixtures thereof. Preferably, the buffer components are water soluble materials such as phosphoric acid, tartaric acids, lactic acid, succinic acid, citric acid, acetic acid, ascorbic acid, aspartic acid, glutamic acid, and salts thereof.

The primary solvent in a vehicle may be either aqueous or non-aqueous in nature. In addition, the vehicle may contain other pharmaceutically-acceptable excipients for modifying or maintaining the pH, osmolarity, viscosity, clarity, color, sterility, stability, rate of dissolution, or odor of the formulation. A preferred pharmaceutical composition of GDNF comprises a therapeutically effective amount of at least one GDNF protein and a pharmaceutically acceptable vehicle. More preferably, the pharmaceutically acceptable vehicle is an aqueous buffer. More preferably, the vehicle comprises sodium chloride at a concentration of about 100 mM to about 200 mM and sodium citrate at a concentration of about 5 mM to about 20 mM. Even more preferably, the vehicle comprises sodium chloride at a concentration of about 125 mM to about 175 mM and sodium citrate at a concentration of about 7.5 mM to about 15 mM. Even more preferably, the vehicle comprises sodium chloride and sodium citrate at a concentration of about 150 mM and about 10 mM, respectively. Most preferably, the GDNF pharmaceutical composition is formulated as a liquid with 10 mM sodium citrate and 150 mM sodium chloride at a pH of 5.0.

The GDNF pharmaceutical composition may contain still other pharmaceutically-acceptable formulation agents for modifying or maintaining the rate of release of GDNF protein product. Such formulation agents are those substances known to artisans skilled in formulating sustained release formulations. For further reference pertaining to pharmaceutically and physiologically acceptable formulation agents, see, for example, Remington's Pharmaceutical Sciences, 18th Ed. (1990, Mack Publishing Co., Easton, Pa. 18042) pages 1435-1712 (the disclosure of which is hereby incorporated by reference).

Once the therapeutic composition has been formulated, it may be stored in sterile vials as a solution, suspension, gel, emulsion, solid, or dehydrated or lyophilized powder. Such formulations may be stored either in a ready to use form, a lyophilized form requiring reconstitution prior to use, or a liquid form requiring dilution prior to use. Preferably, the GDNF pharmaceutical composition is provided in sterile single-use vials at a concentration of 10 mg/mL and stored at a temperature of −2-8° C. until use. Immediately prior to administration, the GDNF protein product should be thawed and appropriately diluted with a sterile citrate buffered saline (pH 5.0) consisting of 150 mM sodium chloride and 10 mM sodium citrate.

In the methods of the present invention, GDNF is chronically administered to a site of dopaminergic dysfunction in the human brain by means of an implantable pump and one or more catheters. The region of a PD patient's brain targeted for chronic delivery of GDNF may be determined by assessing biomarkers of PD disease or disease progression including, but not limited to, the number of TH expressing neurons 2) size of dopamine neuronal cells 3) dopamine metabolite levels 4) dopamine storage, 5) dopamine transport, 6) neuronal dopamine uptake, 7) dopamine transporter binding, 8) quantal size of terminal dopamine release, 9) rate of dopamine turnover, 10) TH+ cell count, 11) TH+ innervation density and 12) TH+ fiber density. For instance, GDNF may be infused directly into a region of the human brain which is severely dopamine depleted. The region of a PD patients brain which is severely dopamine depleted and, therefore, a target for chronic delivery of GDNF may be determined by neuroimagery of the brain, or regions thereof. The neuroimagery technique used to determine the site of chronic infusion of GDNF may be selected from the group consisting of $^{18}$F-fluorodopa positron emission tomography ($^{18}$F-dopa PET)[13], $^{123}$I-2β-carboxymethoxy-3β-(4-iodophenyl)tropane uptake on single-photon emission tomography ($^{123}$I-β-CIT SPECT), and similar techniques. In a preferred embodiment of the present invention, GDNF is infused directly into at least one dopaminergic dysfunctional putamen of a PD patient. Even more preferably, GDNF is infused directly into the posterior region of at least one dopaminergic dysfunctional putamen of a PD patient. Most preferably, GDNF is infused directly into at least one dopaminergic dysfunctional postero-dorsal putamen of a PD patient.

A number of drug delivery apparatus, catheters, catheter systems and combinations thereof have been developed for the dispensing of medical substances to specific sites within the body and are all readily available to those skilled in the art for use in the methods of the present invention. Therefore, one may use prior art drug delivery devices, catheters, and catheter systems for delivering the GDNF compositions to the target site of the brain of the patient at specified concentrations and/or at specified times and/or at different delivery rates. By way of illustration and not limitation, in the methods of the present invention one may use the technology described in U.S. patent Publication No. US20030120262, US20030208184, or US20030225372 or U.S. Pat. No. 4,931,050, 4,838,887, 5,207,666, 4,714,462, 5176,641; 3,923,060, 4,003,379, 4,588,394, 4,447,224, 5,575,770, 4,978,338, 5,908,414, 5,643,207, 6,589,205 or 6,592,571. The entire disclosure of each of these U.S. Patent Applications and U.S. Patents is hereby incorporated by reference into this specification. A preferred drug delivery apparatus useful in the context of the present invention includes one described in U.S. Pat. No. 5,752,930 or U.S. patent application No. US20030216714 (which are hereby incorporated by reference in their entireties). A more preferred drug delivery apparatus useful in the context of the present invention includes one described in U.S. Pat. No. 6,620,151 (which is hereby incorporated by reference in its entirety). An even more preferred drug delivery apparatus useful in the context of the present invention includes one described in U.S. patent application No. US20030216714 (which is hereby incorporated by reference in its entirety). Most preferably the drug delivery apparatus used in the context of the present invention is one described in U.S. Pat. No. 4,146,029, 4,013,074, or 4,692,147, (which are hereby incorporated by reference in their entireties) commercial embodiments thereof including, but not limited to, the Synchromed® I, Synchromed® EL, and Synchromed® II infusion pumps (Medtronic, Inc., Minneapolis, Minn.).

In another embodiment of the present invention, in conjunction with any of the above or below embodiments, a number of catheters and catheter systems have been developed for the dispensing of agents, such as drugs, to specific sites in the body and are readily available to those skilled in the art for use in the methods of the present invention. By way of illustration and not limitation, in the methods of the present invention one may use the technology described in U.S. patent Publication No. 20030216700, 20030199831, or 20030199829 or U.S. Pat. No. 6,319,241. The entire disclosure of these U.S. Patent Applications and the United States patent is hereby incorporated by reference into this specification.

The methods of the present invention are also achievable by infusion of GDNF utilizing a single port catheter. A single port catheter is a catheter having one hole or port, generally disposed at the distal end of the catheter. Accordingly, a catheter or catheter system useful in the context of the present invention includes, but is not limited to, an intraparenchymal infusion catheter or catheter system described in International Patent Application Publication No: WO 02/07810, WO03/002170, or WO 03/077785, or U.S. Pat. No. 5,720,720, 6,551,290, 6,093,180 or 6,609,020. The entire disclosure of each of these Patent Applications and United States patents is hereby incorporated by reference into this specification.

The methods of the present invention are also achievable by infusion of GDNF utilizing a multiport catheter. A multiport catheter is a catheter having a plurality of infusion holes or ports disposed along the length of the catheter or catheter tip. Generally, a multiport catheter will have said infusion holes or ports longitudinally spaced along the tip length at substantially regular intervals. A multiport catheter therefore may have about 20 to about 60 ports, about 30 to about 50 ports, or about 35 to about 45 ports, along its length or the length of the catheter tip. A catheter useful in the methods of the present invention includes, but is not limited to, an intraputamenal (IPA) multiport catheter having 40 ports arranged 4 per 0.5 mm placed approximately every 90°, about 5 mm length, such as model #10532, manufactured by Medtronic, Inc. (Minneapolis, Minn.), or any catheter substantially similar thereto.

In another embodiment of the methods of the present invention, in conjunction with any of the above or below embodiments, a therapeutically effective dose of GDNF is infused directly into one or both putamen of a human PD patient. The phrase "therapeutically effective dose" or "pharmaceutically effective dose", which are used interchangeably herein, refers to that amount of GDNF sufficient to result in any amelioration, impediment, prevention or alteration of any biological symptom generally associated with a neurodegenerative disorder including, without limitation, PD by one skilled in the relevant art. In a preferred embodiment of the present invention, in conjunction with any of the above or below embodiments, GDNF is directly into a human putamen at a dose of about 1 µg/putamen/day to about 100 µg/putamen/day. More preferably, GDNF is infused directly into a human putamen at a dose of about 5 µg/putamen/day to about 50 µg/putamen/day. Even more preferably, GDNF is infused directly into a human putamen at a dose of about 10 µg/putamen/day to about 75 µg/putamen/day. Even more preferably, GDNF is infused directly into a human putamen at a dose of about 15 µg/putamen/day to about 50 µg/putamen/day. Even more preferably, r-metHuGDNF is infused directly into a human putamen at a dose of about 20 µg/putamen/day to about 45 µg/putamen/day. Even more preferably, r-metHuGDNF is infused directly into a human putamen at a dose of about 25 µg/putamen/day to about 40 µg/putamen/day. Even more preferably, r-metHuGDNF is infused directly into a human putamen at a dose of about 30 µg/putamen/day to about 35 µg/putamen/day. Most preferably, r-metHuGDNF is infused directly into a human putamen at a dose of about 30 µg/putamen/day.

Applicants also disclose herein the use of a pharmaceutically effective amount of GDNF including, but not limited to, r-metHuGDNF, and at least one pharmaceutically acceptable vehicle, excipient, or diluent in the preparation of a pharmaceutical composition for treating cognitive disorders or inhibiting cognitive decline associated with neurodegenerative disorders, including, without limitation, PD and dementia, wherein the composition is for administration to one or both putamen of a human in need thereof via convection-enhanced infusion using at least one implantable pump and at least one catheter. In a preferred use of a pharmaceutically effective amount of GDNF and at least one pharmaceutically acceptable vehicle, excipient, or diluent in the preparation of a pharmaceutical composition for treating cognitive disorders or inhibiting cognitive decline associated with neurodegenerative disorders, including, without limitation, PD and dementia, the composition is for administration to a site of dopaminergic dysfunction within one or both putamen of a human in need thereof via convection-enhanced infusion using at least one implantable pump and at least one catheter. For such uses dopaminergic dysfunction is pre-operatively. In another embodiment of the present invention, in conjunction with any of the above or below embodiments The inventive method has the effect, upon application to parkinsonian patients, of significantly reducing symptoms of Parkinson's disease, the resulting improved condition of the patient continuing for at least 30 months. In particular, a clear improvement of disease-specific symptoms was obtained with the inventive method insofar as motoricity, fine motoricity, and fine dexterity. In addition, mobility and concentration power was increased and reaction time was decreased. Pronunciation, facial expressiveness, posture, sense of smell, libido, sexual function, and emotional condition were improved and state of mind was brightened.

In yet another embodiment of the present invention, GDNF can be used as a cognitive enhancer, to enhance learning, particularly as a result of dementias or trauma, or to inhibit cognitive decline and/or dementia, for example, in patients with PD. Alzheimer's disease, which has been identified by the National Institutes of Aging as accounting for more than 50% of dementia in the elderly, is also the fourth or fifth leading cause of death in Americans over 65 years of age. Four million Americans, 40% of Americans over age 85 (the fastest growing segment of the U.S. population), have Alzheimer's disease. Twenty-five percent of all patients with Parkinson's disease also suffer from Alzheimer's disease-like dementia. Applicants have shown here for the first time that chronic intraputaminal administration of GDNF has application in treating or preventing cognitive disorders in humans. In particular, intraputaminal administration of GDNF has application in treating or preventing cognitive disorders and/or Alzheimer's disease-like dementia associated with PD.

EXAMPLES

The following examples, including the experiments conducted and results achieved are provided for illustrative purposes only and are not to be construed as limiting the invention.

Example 1

Unilateral Intraputamenal GDNF Improves Bilateral Motor Functions in Patients with Parkinson's Disease Methods
Subjects Consent from the patients described in Example 1 was obtained in accordance with the FDA and the local University of Kentucky Medical Center Internal Review Board regulations and guidelines. Patients were diagnosed with idiopathic PD according to standard criteria (Hughes, A. J., et al., What features improve the accuracy of clinical diagnosis in Parkinson's disease: A clinicopathologic study?, Neurology, 42:1142-1146 (1992)). Eight men and two women, aged 47 to 70 years (see Table 2), with moderate to severe idiopathic PD (Hoehn and Yahr Stage 3-4) were selected for the study. Primary symptoms were rigidity and bradykinesia with disease duration ranging from 4.8 to 15.4 years (Table 2). Exclusion criteria included the presence of clinically significant depression or dementia, concomitant disease likely to interfere with the study, prior surgery for PD, drug or alcohol dependence/abuse, and inability or unwillingness to comply with long-term follow-up. Premenopausal subjects had to agree to abstinence or use of barrier methods of birth control during the study unless surgically sterile. No patients had had prior exposure to neuroleptics or used selegiline for two months prior to implantation of the catheter. For the two months prior to the study patients had had stable symptoms and had been maintained on a constant regimen of anti-PD medications consisting of L-dopa and/or a dopamine agonist (range 300-2500 mg/day levodopa equivalents, see Nutt, J. G., et al., (2003)); a catechol-o-methyltransferase inhibitor (COMT) had been used by two subjects and amantadine by two patients. No changes were made in patients' anti-PD drug regimens during the course of the study.

TABLE 2

Patient Data, Side-Effects, and Other Effects of GDNF

| | Patient # | | | | |
|---|---|---|---|---|---|
| | 1 | 2 | 3 | 4 | 5 |
| Age (years) | 70 | 54 | 49 | 61 | 48 |
| Duration of disease (years) | 5.6 | 5.2 | 11.4 | 15.4 | 7.9 |
| L-Dopa equivalents/day | 450 | 300 | 1275 | 902 | 750 |
| Change in medications after 6 mo. | | | | | |
| Taste Abnormalities | | | | | |
| Lhermitte's | | + | | | |
| Hyponatraemia | | | | | |
| Improved Bladder Control | | | | | |
| Recovery of Sexual Function | | | | | |
| Improvement in Taste/Smell | | | | | + |
| Reduction in Hypomimia* (Off)* | + | | + | | + |
| Reduced Hypophonia (Off and On)* | + | + | | + | + |
| Improved Postural Stability (Off)* | + | + | + | + | + |
| Decreased End-of-Dose Fluctuations* | | + | + | | + |
| Decreased Dyskinesia* | | | + | | |
| DELIVERY SYSTEM EFFECTS | | | | | |
| Headaches | + | + | + | + | + |
| MRI Changes | + | + | + | + | + |
| Pump Related Discomfort | + | + | + | + | + |

| | Patient # | | | | |
|---|---|---|---|---|---|
| | 6 | 7 | 8 | 9 | 10 |
| Age (years) | 50 | 63 | 69 | 68 | 47 |
| Duration of disease (years) | 4.8 | 6.2 | 12.2 | 11.8 | 6.8 |
| L-Dopa equivalents/day | 700 | 1775 | 1200 | 2500 | 500 |
| Change in medications after 6 mo. | | | | | |
| Taste Abnormalities | + | | | | |
| Lhermitte's | + | | | | |
| Hyponatraemia | | | | | |
| Improved Bladder Control | | | | | |
| Recovery of Sexual Function | | | | | |
| Improvement in Taste/Smell | | | | | |
| Reduction in Hypomimia* (Off)* | + | + | + | + | + |
| Reduced Hypophonia (Off and On)* | + | + | | | |
| Improved Postural Stability (Off)* | + | + | + | | |
| Decreased End-of-Dose Fluctuations* | + | | + | + | + |
| Decreased Dyskinesia* | | | | + | + |

TABLE 2-continued

Patient Data, Side-Effects, and Other Effects of GDNF

| DELIVERY SYSTEM EFFECTS | | | | | |
|---|---|---|---|---|---|
| Headaches | + | + | + | + | + |
| MRI Changes | + | + | + | + | + |
| Pump Related Discomfort | + | + | + | + | + |

Duration of disease is from onset of symptoms to week prior to surgery.
L-Dopa Equivalents based on Nutt, J. G., et al., (2003).
Reduction in hypomimia (question 19, section 3 UPDRS).
Reduced hypophonia (question 5, section 2 and question 18, section 3 UPDRS).
Improved postural stability (questions 29 & 30, section 3 UPDRS).
Decreased end of dose fluctuations (questions 36-39, section 4 UPDRS).
Decreased dyskinesia (questions 32-34, section 4 UPDRS).

Surgical Procedures

Figure 1B:
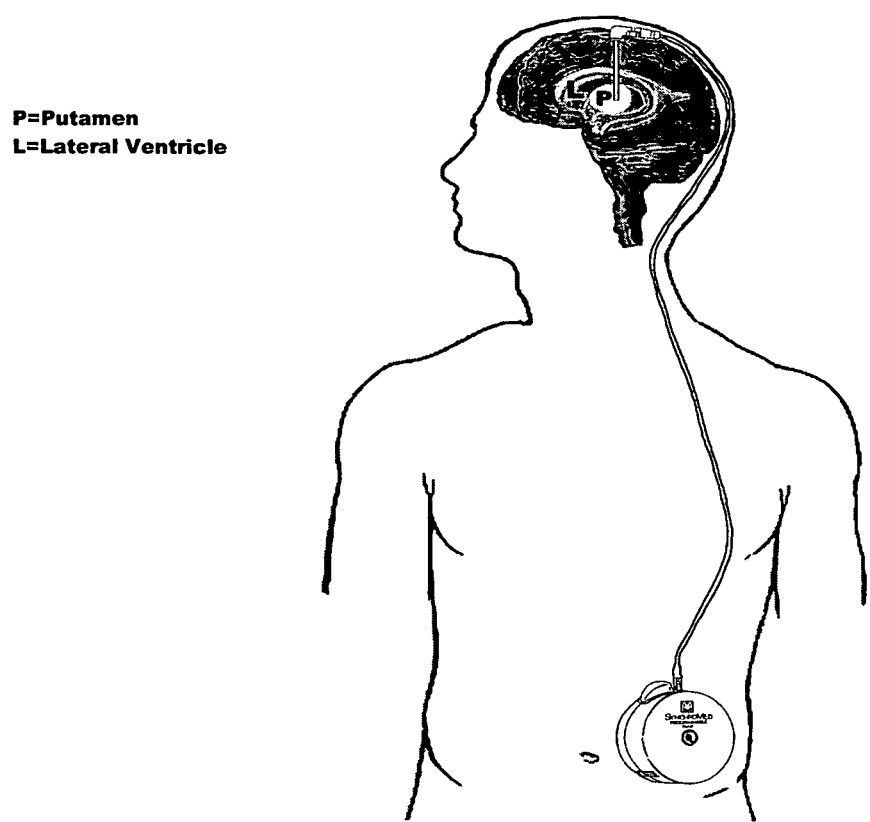

Each patient had an MRI-based stereotactic implantation of an intraputamenal (IPA) multi-port catheter (1.65 mm O.D. diameter, 40 holes, 4 per 0.5 mm placed every 90°, 5 mm length; Medtronic, Inc., Model #10532) and SynchroMed® pump (Medtronic, Inc., Model #8626L-18) contralateral to the most affected side (see FIG. 1(a) and FIG. 1(b)). For each patient, a Leksell headframe was applied and a 1 mm slice MRI scan was performed. Targeting of the catheter placement was achieved using the Leksell Surgi Plan®(Copyright© 1991-2003 Elekta Instruments AB Stockholm, Sweden). Following standard stereotactic surgical procedures, the IPA catheter was inserted into the medial putamen. The citrate buffered saline-primed infusion pump was implanted subcutaneously in the ipsilateral lower quadrant abdominal wall and a catheter was tunneled to connect the pump to the indwelling IPA catheter. Locations of all catheters are schematically shown in FIG. 1(a). A schematic of the infusion system is seen in FIG. 1B. A postoperative MRI and posterior-anterior and lateral x-rays of the skull, chest and abdomen were performed 24 hours after surgery to confirm placement of the catheter tip, continuity of the connections, and to detect putamenal hemorrhage. All catheters were seen to be within the putamen (see FIG. 1a).

GDNF Treatment

The recombinant-methionyl human glial cell line-derived neurotrophic factor (r-metHuGDNF) was prepared by Amgen, Inc. (Thousand Oaks, Calif.). The r-metHuGDNF was stored in single-use vials in a buffer of 10 mM citrate and 150 mM sodium chloride (CBS) at pH 5.0. At implantation, the pump was filled with preservative-free CBS and programmed to infuse at 133 µL/day and pump refills occurred monthly. The pump was programmed to infuse at a continuous basal infusion rate of 2 µl/hour. Small bolus injections (21.3 µl delivered in 117 seconds) were delivered every 6 hours to supplement the basal rate and to increase the brain area affected by the drug. At the end of week four post surgery, r-metHuGDNF infusion began, with dose escalations at eight week intervals from 3 µg/day to 10 µg/day to 30 µg/day. Solution concentrations of GDNF were adjusted to deliver the same amount of fluid (133 µl) per day. After 24 weeks of infusion, the remaining r-metHuGDNF was removed from the pump and the pump was filled with CBS. Due to the slow drug infusion rate, and the length of catheter tubing between the pump and the tip of the putamenal catheter, it takes approximately one week for r-metHuGDNF in the tubing to clear. Therefore, a total washout period of five weeks was needed to assess the effects of four weeks of trophic factor withdrawal. After the drug washout, patients had the option of reinstating GDNF treatment at the highest previous tolerated dose level for an extended period. All ten subjects requested continuation of the GDNF infusions.

Clinical Testing and Follow Up

Clinical evaluations were based on 1) UPDRS Total ON and OFF Scores, 2) UPDRS Motor ON and OFF Scores and 3) the Clinical Assessment Program for Surgical Interventional Therapies in Parkinson's Disease CAPSIT-PD (Defer, G-L., Core assessment program for surgical interventional therapies in Parkinson's disease (CAPSIT-PD). Mov Dis., 14:572-584 (1999)). All patients were evaluated using total UPDRS and CAPSIT-PD timed motor tests, and were requested to keep a personal diary. Required visits were scheduled weekly during the first four weeks of the study after pump implant. Thereafter, visits were scheduled monthly through the 24 weeks of GDNF therapy with a final follow-up visit to assess the effects of GDNF washout.

Statistical Methods

For the UPDRS endpoints, comparison of mean responses across time was based on a linear mixed model with post hoc comparison of means based on Fisher's protected least significant differences procedure. Confidence intervals for the percent change from baseline to the 24 week follow-up were obtained by the delta method and are based on a t-distribution with 9 degrees of freedom. For the CAPSIT-PD endpoints some patients could not complete some tasks in which case a score of 90 seconds was assigned to the Stand-Walk-Sit task and 30 seconds was assigned to the Hand-Arm movement test. Comparison of the distribution of responses was based on Friedman's chi-square statistic with post hoc comparison of means based on Fisher's protected least significant differences procedure applied to the ranks across time determined on a patient by patient basis. Control of the Type I error rate for testing each week of follow-up to the baseline week was obtained by applying the Bonferroni-Holm procedure (Holm, S. A simple sequentially rejective multiple test procedure. Scand. J. Statistics, 6: 65-70 (1979)). Statistical significance was determined at the 0.05 level.

Results

Testing was conducted in an operationally-defined OFF condition: (i) anti-PD medications withheld for 2.5 times the duration of each drug's predicted serum half life, and (ii) prior to the subject's first dose of medication on the day of testing. Total UPDRS scores were significantly improved by 16, 20 and 33% in the OFF condition at 8, 16, and 24 weeks, respectively (Table 3). Total UPDRS scores in the ON condition were also improved by 26, 23, and 34% at 8, 16, and 24 weeks post-GDNF, respectively. ON testing was performed within six hours after the subject's first dose of anti-PD medication for the day. These improvements were maintained over the five weeks after discontinuation of the highest-dose infusion (30 mcg/day). The 95% confidence intervals (CI) for % change from baseline at 24 weeks are given in Table 4, which support the clinical significance of the GDNF effects at 24 weeks. UPDRS (Part III) Motor scores in OFF were also significantly improved by 13, 20, and 30% at 8, 16, and 24 weeks post-GDNF, respectively. UPDRS Motor scores in ON were seen to be significantly improved by 35, 30, and 30% at 8, 16, and 24 weeks post-GDNF, respectively. The 95% confidence intervals (CI) for % change from baseline at 24 weeks are given in Table 4, which support the clinical significance of the GDNF effects at 24 weeks. UPDRS Motor scores remained significantly improved in OFF and ON after washout. In addition, eight patients showed improved postural stability in OFF, seven reported decreased end-of-dose fluctuations and three experienced decreased dyskinesia (Table 2). Other motor/sensory improvements included reduced hypophonia (OFF and ON) in six patients, reduced hypomimia in eight patients and improved taste and smell reported by one patient (Table 2). The observed reduction in bradykinesia was supported by the CAPSIT-PD measures of timed Hand-Arm and SWS tests. The results of testing in the OFF and ON condition are seen in Table 3. Bilateral axial movements including balance and gait were measured in SWS testing and were improved by 26% in OFF at six months post-GDNF. Bilateral improvements were also evident in the Arm-Hand test measuring movement speed between two points 30 cm apart. Performance times of the Arm-Hand test were significantly faster in both ON and OFF on both the contralateral and ipsilateral sides to the site of intraputamenal infusion, with significant improvements ranging from 31-44% at 16 and 24 weeks post-GDNF.

Safety and Side Effects

The unilateral pump implantation procedure was safe, with few adverse events reported by all ten patients (Table 2). There was general discomfort from the pump, which was experienced by all ten subjects immediately following surgery and sporadically thereafter. All patients experienced headaches the day following surgery, which resolved and did not reoccur. The MRI changes consisted of a halo of increased signal intensity on T2-weighted images less than 1 cm in thickness around the catheter. There was no change in body

TABLE 3

GDNF Improves UPDRS and CAPSIT Measures

| Tests | | BASELINE | P* | 8 WEEKS 3 μg/day | P+ |
|---|---|---|---|---|---|
| Total UPDRS | OFF | 64 ± 5 | <.0001 | 54 ± 4 (−16%) | 0.011 |
| | ON | 47 ± 3 | 0.0005 | 35 ± 3 (−26%) | 0.0011 |
| Motor UPDRS | OFF | 40 ± 4 | 0.0004 | 35 ± 3 (−13%) | 0.0291 |
| | ON | 23 ± 2 | 0.0201 | 15 ± 3 (−35%) | 0.0075 |
| CAPSIT Stand, Walk, Sit | OFF | 39 ± 8 | 0.0464 | 37 ± 10 (−5%) | 0.1741 |
| | ON | 22 ± 5 | 0.1032 | 19 ± 3 (−14%) | — |
| CAPSIT Contralateral Hand/Arm | OFF | 18 ± 2 | 0.0002 | 15 ± 3 (−17%) | 0.0792 |
| | ON | 13 ± 2 | 0.0004 | 12 ± 2 (−8%) | 0.2680 |
| CAPSIT Ipsilateral Hand/Arm | OFF | 15 ± 2 | 0.0005 | 12 ± 1 (−20%) | 0.0348 |
| | ON | 12 ± 2 | 0.0005 | 10 ± 1 (−17%) | 0.0242 |

| Tests | | 16 WEEKS 10 μg/day | P++ | 24 WEEKS 30 μg/day | P+++ | WASHOUT | P++++ |
|---|---|---|---|---|---|---|---|
| Total UPDRS | OFF | 51 ± 4 (−20%) | 0.0014 | 43 ± 5 (−33%) | <0.0001 | 53 ± 4 (−19%) | 0.0037 |
| | ON | 36 ± 5 (−23%) | 0.023 | 31 ± 4 (−34%) | <0.0001 | 34 ± 4 (−30%) | 0.0004 |
| Motor UPDRS | OFF | 32 ± 3 (−20%) | 0.0034 | 28 ± 4 (−30%) | <0.0001 | 33 ± 3 (−18%) | 0.0038 |
| | ON | 16 ± 4 (−30%) | 0.0166 | 16 ± 4 (−30%) | 0.0090 | 14 ± 3 (−39%) | 0.0027 |
| CAPSIT Stand, Walk, Sit | OFF | 29 ± 7 (−26%) | 0.0491 | 29 ± 9 (−26%) | 0.0012 | 31 ± 8 (−21%) | 0.0491 |
| | ON | 15 ± 1 (−32%) | — | 14 ± 1 (−36%) | — | 14 ± 1 (−32%) | — |
| CAPSIT Contra-lateral Hand/Arm | OFF | 12 ± 2 (−43%) | 0.0037 | 10 ± 2 (−44%) | <.0001 | 14 ± 3 (−22%) | 0.0009 |
| | ON | 9 ± 1 (−31%) | <.0001 | 8 ± 2 (−38%) | <0.0001 | 10 ± 2 (−23%) | 0.0010 |
| CAPSIT Ipsilateral Hand/Arm | OFF | 10 ± 1 (−33%) | <.0001 | 9 ± 1 (−40%) | <0.0001 | 11 ± 1 (−27%) | 0.0004 |
| | ON | 8 ± 1 (−33%) | <.0001 | 8 ± 1 (−33%) | <0.0001 | 8 ± 1 (−33%) | <.0001 |

Baseline UPDRS scores for each patient are the means of three pre-GDNF determinations at −1, +1 and + 4 weeks following catheter implantation.
UPDRS measures are means ± SEM.
CAPSIT measures are in seconds ± SEM.
*P value for comparing response across time.
P values for post hoc comparisons:
+ 8 weeks vs. baseline;
++ 16 weeks vs. baseline;
+++ 24 weeks vs. baseline;
++++ washout vs. baseline

TABLE 4

95% Confidence intervals after 24 weeks of GDNF therapy

| | | | 95% CI | |
|---|---|---|---|---|
| Endpoint | State | % Improvement | Low | High |
| Total UPDRS | Off | 33% | 18% | 47% |
| Total UPDRS | On | 34% | 16% | 51% |
| Motor UPDRS | Off | 30% | 15% | 48% |
| Motor UPDRS | On | 30% | 5% | 61% |

Confidence intervals for percent change from baseline to improvement in Table 4 at 24 weeks.

weight during the trial. Adverse event frequencies were: catheter re-placement (1/10), infection (0/10), pump failure (0/10), hemorrhage (0/10), blood chemistry abnormalities (0/10) and delivery system complications/disconnections (0/10). Two subjects reported transient Lhermitte's symptoms on 1-2 occasions. None of the subjects reported nausea, anorexia, vomiting or weight change as was seen by Nutt, et al., (2003). In addition, none of our ten subjects experienced hyponatraemia or alterations in antidiuretic hormone (ADH).

The sustained improvements in all ten subjects are consistent with extensive preclinical data suggesting GDNF efficacy in treating PD. The 95% confidence limits for the total and motor UPDRS scores in ON and OFF further support the clinical significance of the results. Decreases over baseline in the total and motor UPDRS scores after one-month washout indicate that the positive effects of GDNF may persist for at least four weeks after GDNF withdrawal. However, these persistent gains may be less in magnitude compared to the maximum benefit observed during active GDNF infusion. This is consistent with prior studies in animal models of PD (Grondin, R., et al., (2002); Grondin, R., et al., (2003), Hebert, M. A., (1997)).

Sustained and consistent placebo effects do not typically occur in PD subjects (14,15) and patients with PD do not spontaneously improve over time making these confounds less likely explanations for the time course of improvements we observed. Strikingly, significant effects were observed in all subjects receiving intraputamenal infusion of GDNF. Such consistent effects have not been seen in other treatments for PD such as DBS or fetal cell transplants (Krack, P., et al., Five-year follow-up of bilateral stimulation of the subthalamic nucleus in advanced Parkinson's disease, N. Engl. J. Med., 349:1925-1934 (2003); Olanow, C. W., et al., A double-blind controlled trial of bilateral fetal nigral transplantation in Parkinson's disease, Ann. Neurol. 54:403-414 (2003)). Eight subjects in this study showed improved postural stability, six of the ten patients had improved speech (reduced hypophonia) and seven patients exhibited decreased hypomimia. The quality of ON time was improved by decreased symptom fluctuations in seven subjects. While dyskinesias were not prominent in this patient group, they were reduced in three subjects. All of the patients also reported an increased sense of well-being (manuscript in preparation), suggesting an additional effect of intraputamenal GDNF.

Example 2

Treatment of Parkinson's Disease in Humans with Convection-Enhanced Infusion of GDNF into the Putamen Study Design Five patients with idiopathic, L-dopa responsive PD who were poorly controlled on optimal medical therapy were identified. The first patient (P1) had predominantly unilateral disease affecting the left side and underwent contralateral putamenal implantation of catheter and pump for r-metHuGDNF delivery. The remaining patients (P2-5) had bilateral disease and bilateral putamenal implantations of delivery systems. The precise region of the dorsal putamen to be targeted for infusion was determined by co-localization studies using $^{18}$F-dopa PET and MR images. Under MRI guidance, single-port catheters were placed into the dorsal putamen, the site of maximal loss of $^{18}$F-fluorodopa signal (confirmed by PET in all subjects). Pump placement and stereotactic surgery were tolerated well by all patients. However, there were some complications. P1 required perioperative repositioning of the catheter to center exactly within the dorsal putamen. This was achieved successfully on a second pass during the surgical procedure. In addition, patient 4 developed a wound infection related to the pumps and connection tubing that was successfully treated with explantation of the extracranial devices, antibiotics and re-implantation within 4 weeks.

Patients

Five PD patients were included in this pilot study. Ethical approval was obtained from the local ethics committees both at Frenchay Hospital and the Hammersmith Hospitals Trusts and all participants signed full consent forms. All patients were diagnosed as suffering from idiopathic PD according to standard criteria (brain bank criteria). Patients were selected for surgery when they were suffering significant functional impairment despite optimal medical therapy. Exclusion criteria included women of child-bearing age, age over 65, the presence of clinically significant depression, or systemic disease or inability or unwillingness to comply with long-term follow-up.

Surgery

Sub cortical nuclei were localized and targeted using high-resolution MR images acquired under strict stereotactic conditions. Under general anesthesia, a modified Leksell stereotactic frame was affixed parallel to the orbito-meatal plane. The anterior (AC) and posterior (PC) commisures were identified in a mid-sagittal planning scan. Axial images 2 mm thick were acquired parallel to the AC-PC plane and coronal images orthogonal to these then obtained. Using magnified hard copies of the MRI scans the inversion recovery scans were overlaid with the inverted T2 images to enhance the definition of the putamenal boundaries in both planes. Using the PET images, the area of the postero-dorsal putamen with the lowest $^{18}$F-dopa uptake was targeted for infusion; stereotactic target coordinates were recorded and a trajectory planned. The following day, surgery was performed under general anesthesia. Under stereotactic conditions, 1 mm diameter guide tubes were implanted to a point above the putamen target over a guide rod. A 0.6 mm guide wire was introduced down the guide tube to target, following which the patients underwent repeat MR/CT imaging to verify target localization. The guide wire was then replaced with a 0.6 mm diameter catheter introduced to target. r-metHuGDNF primed SynchroMed pumps (Medtronic Inc, Minneapolis) were implanted in the upper abdominal region, subcutaneously in the first patient, and subfascially (beneath the anterior rectus sheath) in the subsequent cases; subfascial placement reduced the pump profile in the abdomen and improved cosmetic appearance. Catheters were tunneled connecting the pumps to the indwelling 0.6 mm intraparenchymal brain catheters.

Convection-enhanced infusion into the targeted brain tissue was achieved in this study by pumping drug at a relatively high rate through the smallest possible catheter having a single port at its distal end. Otherwise, drug emerging from a single port in the distal end would tend to travel up the path of least resistance, i.e., up the catheter/tissue interface. Because the flow up this space is proportional to the radius squared, even small increases in catheter size would be expected to reduce the resistance outside the catheter, therefore reducing the pressure gradient and bulk flow into the tissue substantially. Additionally, the smallest possible catheter is preferred since catheter placement would be expected to cause tissue trauma and local necrosis resistance to flow would be lower along the catheter tract. Therefore, it follows that a smaller catheter would result in less tissue damage and less drug flowing back along the catheter tissue interface to the cortex and entering the CSF space. On the other hand, with larger catheters and slower infusion rates, fluid penetration into the tissues becomes solely dependent upon diffusion down a concentration gradient, which due to the size of the GDNF molecule will be very limited. This is supported by Chen et al. (J. Neurosurg 90:315-320, 1999—see appendix), who demonstrate in a rat model that infusing protein into the striatum with a 0.4 mm catheter results in 5% loss of infusate through leak back along the catheter, and by increasing the diameter to 0.6 mm, the loss increases to 35%. In this study, increasing the infusion rate beyond about 6 µl per hour, increased leak back and loss of infusate and infusate concentration had no effect on the volume of distribution.

r-metHuGDNF Production and Infusion

Recombinant-methionyl human glial cell line-derived neurotrophic factor (r-metHuGDNF) was prepared by Amgen Inc. This protein was produced in *Escherichia coli* cells that contain an expression plasmid with a DNA insert encoding mature human GDNF, with an addition of an amino terminal methionine. r-metHuGDNF is liquid formulated with 10 mM sodium citrate and 150 mM sodium chloride at a pH of 5.0. It was supplied in single-use vials at a concentration of 10 mg/mL. Following implantation, the SynchroMed pumps were programmed to deliver a continuous infusion of 14.4 µg of r-metHuGDNF per putamen per day at rate of 6 µl per hour. The pumps were refilled monthly with fresh solution. The low concentration of r-metHuGDNF was maintained for a period of 8 weeks. At 2 months the pumps were refilled with fresh solution of higher concentration and programmed to deliver 43.2 µg of r-metHuGDNF per putamen per day at a rate of 6 µl per hour. Providing good tolerance and no side effects, this dose was to be maintained for the duration of the trial. However, due to the development of high-signal MRI changes of uncertain significance, the infusion parameters were altered to deliver lower doses (10.8-14.4 µg of r-metHuGDNF) at lower rates (2-6 µl per hour), in attempt to establish safe and clinically effective parameters, with repeat MRI monitoring at regular intervals. Between 12 and 18 months, all patients received a continuous infusion of 14.4 µg of r-metHuGDNF per putamen per day at rate of 6 µl per hour. At 18 months the dose of GDNF was increased to 28.8 µg per putamen per day at rate of 6 µl per hour, and remained so until 24 months or longer except in P4 who reverted back to 14.4 µg at 20 months.

Clinical Evaluation and Follow-Up

Clinical evaluations were based on the Core Assessment Program for Intracerebral Transplantations (CAPIT)(Langston, J. W. et al., Core assessment program for intracerebral transplantations (CAPIT). *Mov Disord.*, 7, 2-13 (1992)) a validated protocol for evaluating surgical treatments of idiopathic PD. All patients were evaluated on the Unified Parkinson's Disease Rating Scale (UPDRS) and underwent timed motor tests at baseline, 3, 6, 12, 18 and 24 months. Assessments were performed in both off and on medication states. Before they were assessed off medication, patients fasted and medications were withdrawn overnight. The same assessments were then repeated after administration of L-dopa when the patients were "on".

Health-Related Quality of Life Outcome Measurement and Follow-Up

Patients were also assessed using validated quality of life questionnaires: the 39-item Parkinson's Disease Questionnaire (PDQ 39) and the 36-item Medical Outcomes Study short form health survey (SF-36) were used before surgery and after 3, 6, 12, 18, and 24 months. Descriptive statistics (mean, standard deviation, range, 95% confidence interval) were obtained for each variable. Comparisons over time were made using Student's paired-samples t test.

Neuropsychological Evaluation and Follow-Up

Also evaluated were changes in medication (L-dopa equivalents) requirement and neuropsychology, which contained tests of verbal intellect, verbal and visual memory, attention, executive function, anxiety and depression as has been previously described (McCarter, R. J., et al., Cognitive functioning after subthalamic nucleotomy for refractory Parkinson's disease. *J. Neurol. Neurosurg. Psychiatry*, 69: 60-66 (2000)). The battery of cognitive tests used was designed to minimize the possible confounding effects of both slowness of movement and movement difficulty on cognitive test results. Friedman's Related Samples test was used to evaluate the significance of change over time in the rating scores. All analyses were performed in SPSS. Four of the patients (all of the bilateral cases) underwent pre-operative neuropsychological assessment. All five patients were assessed at 12 and 24 months post implantation. The significance of changes in cognitive test performance was evaluated using confidence intervals derived from the standard error of prediction around the predicted true score at baseline (Lord, F. M. and Novick, M. R. Statistical theories of mental test scores. Reading, Mass.: Addison-Wesley, (1968); Atkinson, L. Three standard errors of measurement and the Wechsler Memory Scale—Revised. *Psychological Assessment: A journal of consulting and clinical psychology*, 3:136-138 (1991)). A significant change was inferred if a score at either 12 or 24 months fell outside of the confidence interval of the baseline score (for the unilateral case the baseline score was at 12 months and change scores were inferred for performance at 24 months). In addition, a PD control group consisting of 18 patients who had undergone other forms of surgery for PD was used to establish the effect of repeat cognitive assessment over a 12 month period. For each patient in this group two postoperative neuropsychological assessments were available. This control group was comparable with the GDNF patient group in terms of years of education, age at surgery, duration of PD at surgery and NART estimated FSIQ ($p > 0.05$).

Scanning Procedures and Image Analysis $^{18}$F-dopa PET provides a measure of synaptic amino acid decarboxylase (AADC) activity and hence acts as an in vivo marker of dopamine storage and the functional integrity of dopamine terminals. Previous human and animal lesion studies have demonstrated that striatal $^{18}$F-dopa PET correlates with nigral cell numbers, dopamine content in striatal terminals (Garnett, et al., Dopamine visualized in the basal ganglia of living man, *Nature*, 305:137-138 (1983); Martin et al., Nigrostriatal function in humans studied with positron emission tomography. *Annals of Neurology*, 26:535-542 (1989); Brooks et al., Differing patterns of striatal $^{18}$F-dopa uptake in Parkinson's disease, multiple system atrophy, and progressive supranuclear palsy. *Annals of Neurology*, 28:547-555 (1990b); Pate et al., Correlation of striatal fluorodopa uptake in the MPTP monkey with dopaminergic indices. *Annals of Neurology*, 34: 331-338 (1993) and the UPDRS off medication (Morrish, et al., Measuring the rate of progression and estimating the preclinical period of Parkinson's disease with [18F]dopa PET. *Journal of Neurology, Neurosurgery & Psychiatry*, 64: 314-319 (1998)), in particular, with the bradykinesia and rigidity sub scores (Otsuka, et al., Differences in the reduced 18F-Dopa uptakes of the caudate and the putamen in Parkinson's disease: correlations with the three main symptoms, *Journal of the Neurological Sciences*, 136: 169-173 (1996)). Furthermore, it is possible to demonstrate progressive decline of striatal $^{18}$F-dopa uptake in patients with PD over time (Morrish, et al., 1998; Morrish, et al., An [18F] dopa-PET and clinical study of the rate of progression in Parkinson's disease. *Brain*, 119 (Pt 2), 585-591 (1996)). $^{18}$F-dopa PET was used here to assess striatal dopamine terminal function in five PD patients receiving chronic intra-striatal GDNF infusions.

The patients had $^{18}$F-dopa PET pre-operatively, and at 6, 12, 18, and 24 months postoperatively using an ECAT EXACT HR++ camera (CTI/Siemens 966; Knoxville, Tenn.) in 3D acquisition mode following withdrawal from medication for at least 12 hours. Patients received 150 mg of carbidopa and 400 mg of entacapone; 1 hour later 111 MBq of $^{18}$F-dopa in normal saline was administered as an intravenous bolus at the start of scanning. The images were acquired in 3D mode as 26 time frames over 94.5 minutes (1×30 seconds, 4×1 min, 3×2 min, 3×3 min and 15×5 mins). Parametric images of $^{18}$F-dopa influx constants (Ki) were generated from time frames 25.5 to 94.5 minutes post injection using in house software based on the MTGA approach of Patlak and Blasberg (Brooks, D. J., The relationship between locomotor disability, autonomic dysfunction, and the integrity of the striatal dopaminergic system in patients with multiple system atrophy, pure autonomic failure, and Parkinson's disease, studied with PET. *Brain,* 113 (Pt 5) 1539-1552 (1990a); Rakshi, J. S. et al., Frontal, midbrain and striatal dopaminergic function in early and advanced Parkinson's disease A 3D [(18)F]dopa-PET study. *Brain,* 122 (Pt 9): 1637-1650 (1999); Patlak, C. S. & Blasberg, R. G., Graphical evaluation of blood-to-brain transfer constants from multiple-time uptake data. Generalizations. *J. Cereb. Blood Flow Metab.,* 5: 584-590 (1985)). Occipital counts from the same time frames were used to generate the tissue reference input function. Integrated images (time frames 25.5-94.5) were used to identify the parameters required to transform the Ki images into standard stereotaxic MNI space. The transformation matrix was then applied to the Ki images. After normalization a gaussian filter (6×6×6 mm) was applied. Mean voxel values of the normalized Ki images were compared throughout the midbrain and basal ganglia at baseline, 6, and 12 months postoperatively using a paired Student's t-test in SPM99 after application of a mask to eliminate cortical signals and so reduce the number of statistical comparisons. Any regional increases in $^{18}$F-dopa uptake could subsequently be defined as a volume of interest and the mean Ki values for those volumes extracted using the appropriate SPM tool (Brett, M., et al., Region of interest analysis using an SPM toolbox, *NeuroImage,* 16 (2002)).

The integrated images were subsequently co-registered to each patient's MRI scan for region of interest (ROI) analysis. All MRIs had been previously reformatted in the AC-PC plane. The subsequent transformation matrix was then applied to individual Ki images in order to transform them into the individual MRI space. Regions of interest (ROIs) were traced on the MRI and included the head of the caudate and the dorsal putamen which was divided into anterior and posterior halves. The position of the catheter tip was also calculated relative to the AC-PC line and an oval region of interest (6 mm×12 mm) centred at the tip location in the axial plane. The ROI was then copied onto 2 planes either side of the slice containing the calculated tip location, creating a 12 mm×6 mm×5 mm (0.36 cc) volume of interest centered on the catheter tip. The regions of interest were then used to sample $^{18}$F activity on the parametric image. In the 4 patients operated on bilaterally, the mean Ki values for the left and right regions of interest were averaged to produce one Ki value for each of the five ROIs per scan. Only the ROIs from the operated right side of the patient who received unilateral surgery were included in the analyses. The patient's Ki values were then subjected to a paired Student's two-tailed t test.

Lack of Adverse Effects of r-metHuGDNF Infusion

Surprisingly, side effects due to r-metHuGDNF infusion itself were very limited. There was no nausea, anorexia, vomiting or weight loss reported as in the previous intraventricular trial (Kordower, J. H. et al., 1999). There were no haematological or blood chemistry abnormalities. At the high dose (43.2 μg/putamen/day), 3 subjects reported abnormalities of taste and smell (soapy or metallic), 2 subjects reported that their dreams had become abnormally vivid, and 4 subjects described a Lhermitte's phenomenon (tingling passing from the neck down through the arms and sometimes onto the trunk and down the legs provoked by neck flexion). None of these effects necessitated immediate dose cessation or reduction, and all remitted (except for occasional, mild Lhermitte's sign) after the dose change discussed below that was instituted after the appearance of a high-density signal on MRI (end of month 3). The Lhermitte's events were mild, intermittent, non-distressing; and most frequently occurred at the higher dose; and in fact it was often described as "pleasurable".

In all patients, T2 MR images showed a region of high-signal intensity around the tips of the catheters. This response varied between patients, and even between the two hemispheres in bilaterally implanted cases. The signal change was most evident following the dose escalation of r-metHuGDNF. Uncertainty as to the relevance of these changes, led to a reduction of r-metHuGDNF delivery back to 14.4 μg/putamen/day for all patients between 3 and 6 months that resulted in a substantial reduction of the high signal.

Efficacy of r-metHuGDNF Infusion

Improvement in patients' parkinsonian symptoms and signs were evident within 3 months of commencing the infusion and continued to improve throughout the study. Patient diaries revealed that periods of severe immobility, one of the cardinal features of PD that occupied approximately 20% of the waking day prior to surgery, were eliminated completely by 6 months of r-metHuGDNF infusion. At 24-months dyskinesias were reduced significantly by 73% in duration (p<0.05) and were all reported as mild in nature (Table 4). We observed mild dyskinesias in the practically defined off state in P4, who additionally reported short-lived infrequent early morning occurrences. These changes were not due to increases in medication. The study protocol aimed to maintain medication unchanged throughout the first year of r-metHuGDNF treatment. However, P3 had been taking medication on demand due to frequent periods of akinesia at the onset of the study, and needed to reduce his medication as his symptoms improved. Patient P5 had increased sensitivity to L-dopa after GDNF infusion and also needed to reduce his dosage. The other 3 patients needed slight increases in their L-dopa equivalents intake. At 24 months, the mean daily dose of L-dopa equivalents was reduced by 26% (based on a formula as designated by Pahwa, et al. (Pahwa, R., et al., High-frequency stimulation of the globus pallidus for the treatment of Parkinson's disease, *Neurology,* 49: 249-253 (1997)).

The most widely used and validated scale for assessing functional changes in PD is the Unified Parkinson's Disease Rating Scale (UPDRS). In all patients, the rate of symptomatic improvement was maximal in the first 3 months of GDNF infusion and, thereafter, there was slower but sustained improvement throughout the entire 24 months of follow-up. The total UPDRS scores in the clinically defined "off" phase when assessed 12 months following commencement of r-metHuGDNF infusion showed a reduction from baseline of 48%. Although this was a small group of patients, we performed a non-parametric significance test, which showed that this reduction was highly significant across the three time points (P<0.005; Friedman test). The largest effects were seen over the first three months, but the effect persisted throughout the trial. There was also a 45% reduction in total UPDRS scores in the clinically defined "on" phase by 12 months, which followed a similar pattern over time (P<0.002; Friedman test). Although P4's final score was still below baseline, he did show a worsening of symptoms at the twelve-month assessment; this may have been due to an unrelated intercurrent infection.

The patients experienced a mean 41% (p<0.001) improvement in 'off-period' total UPDRS over the first 12 months of follow-up. When the results were broken down, it was clear that these effects in total UPDRS during the "off" phase were reflected by improvements in both activities of daily living (ADL) UPDRS subscale II (P<0.002; Friedman test) and motor UPDRS subscale III scores (P<0.002; Friedman test).

The patients experienced a mean 44% (p<0.0001) improvement in 'off-period' part III motor UPDRS score.

The symptomatic effect at 18-months showed some deterioration from 12 months so the GDNF infusion dose was increased. At 24 months, there was progressive benefit in comparison to 12 months, with the scores in the off-medication state tending towards the baseline best on-medication state. The overall UPDRS scores progressively improved by 57% (p<0.005) and 52% (p<0.005) in both the off and on medication states respectively. The effect of 24 month GDNF infusion on the patients' motor performance (UPDRS part III) was significant in both the off and on medication states, resulting in a 57% (p<0.001) and 48% (p<0.01) score reduction, respectively. There was significant improvement in the patients' functional performance with GDNF infusion, as demonstrated by activities of daily living scores (UPDRS part II), which at 24 months were reduced by 63% (p<0.005) and 58% (P<0.05) in the off and on medication states respectively.

Involuntary movements (i.e. dyskinesias) are a common problem in PD and were suffered by all but one of the patients at the start of the trial. The overall dyskinesia scores (UPDRS subscale IVa) were significantly reduced on medication following r-metHuGDNF infusion for 12 months (P<0.01; Friedman test). No dyskinesias were seen in these patients when off medication. Timed motor tests were assessed and followed the protocol outlined by the Core Assessment Program for Intracerebral Transplantation (CAPIT) (Langston, J. W., et al., 1992). These were also improved in both the "off" and "on" medication states. All the timed motor tests showed significant improvements with GDNF infusion in the off medication state. One patient was unable to complete the stand-walk test without multiple freezing episodes and support whilst in the off medication state preoperatively, but was able to accomplish the task without freezing and support after 12 months of GDNF infusion whilst in the off medication state. Long-term infusion resulted in progressively improved scores for akinesia, rigidity and tremor, impairment of arising from chair, gait and postural instability, when patients were evaluated off medication. GDNF infusion reduced levodopa-induced dyskinesias and motor fluctuations based on complications of therapy scores (UPDRS part IV), which at 24 months were improved by 60% and 29% respectively.

Effect of GDNF Infusion on Quality of Life Measures

The functional status of the patients was assessed using the Parkinson's Disease Questionnaire (PDQ-39) (Peto, V., et al., The development and validation of a short measure of functioning and well being for individuals with Parkinson's disease. *Qual. Life Res.*, 4: 241-248 (1995)) and the 36-item Medical Outcomes Study short form health survey (SF-36) before surgery and after 3, 6, 12, 18, and 24 months. All PDQ-39 domains showed improvement over time. At baseline, the scores were similar to a control PD population with moderate disease (Hoehn and Yahr III) and at 12 and 24 months these scores tended towards a control population with mild disease (Hoehn and Yahr I). At 12 months all dimensions were improved, with bodily discomfort significantly improved (p<0.05). At 24 months all dimensions except social support were improved, with significant improvements for activities of daily living, stigma and cognition (p<0.05). All SF-36 domains were improved at both 12 and 24 months. With time the scores improved towards those for an age-matched healthy population. At 12 months scores for physical functioning and vitality were significantly improved (p<0.05).

Effect of GDNF Infusion on Neuropsychological Measures

The test-retest performance of the PD control group over a 12 month period was assessed using repeated measures 't' tests. No significant improvement in test performance was observed. Significant declines in mean test performance over the 12 month period were observed for the arithmetic subtest of the WAIS-R, immediate and delayed recall of a short story, RAVLT learning and the number of errors obtained on the Tower of London test.

Using the 90% confidence interval of each GDNF patient's baseline score it was found that the majority of patient test scores remain unchanged both at 12 and 24 months. At 12 months there were, however, two significantly improved test scores at the 90% confidence level, one on VIQ and the other on RAVLT learning. These declines occurred in different patients. In addition at 12 months there were two significantly improved test scores, one on VIQ and the other on the delayed recall of a story. Again these significant changes occurred in two different patients. At 24 months there were more significant positive changes in test performance than at 12 months. As with 12 months there were also two test scores that declined, one on VIQ and the other on RAVLT learning. Again these declines occurred in two different patients. The declined VIQ at 24 months was in the same patient who demonstrated a significant decline at 12 months.

The significant improvements in test performance at 24 months occurred on VIQ, immediate and delayed short story recall, RAVLT learning and short delayed recall of the RAVLT. Many of these significant improvements were also evident at the 95% confidence interval. Of these changes improvement in the immediate and delayed recall of a story occurred in one patient and improvement in delayed recall of a story in another patient. One patient demonstrated an improvement in VIQ. Two patients demonstrated an improvement in RAVLT learning with one demonstrating an improvement additionally at the short delayed recall of the RAVLT.

$^{18}$F-dopa PET Scan Changes

Positron emission tomography (PET) scans of $^{18}$F-dopa uptake gives a direct indication of dopamine storage within the brain, and has been used extensively to assess dopamine changes in PD (Morrish, P. K., et al., 1996). Baseline scans revealed that the posterior segment of the putamen in all patients had low $^{18}$F-dopa uptake. These regions of reduced dopamine storage were used to establish the optimal site for placing the catheters for r-metHuGDNF delivery. At 6 months r-metHuGDNF was shown to increase $^{18}$F-dopa uptake by 24.5% (0-49%) within a 0.36 cc ovoid volume around the tip of each catheter. At 12 and 18 months post r-metHuGDNF infusion the same analysis also revealed increases in $^{18}$F-dopa uptake. However, this was complicated by the fact that patient 2 moved considerably during the third scan at 12 months which may have resulted in an under estimate of his true $^{18}$F-dopa uptake. The $^{18}$F-dopa increases at 18 months were significant using a Student's two-tailed t-test in regions where such increases were hypothesized (P=0.021).

Although interrogating a single volume around the tip of each catheter may reveal local changes in $^{18}$F-dopa uptake, changes elsewhere in the putamen or in the midbrain would be missed using this technique. Statistical parametric mapping (SPM) localizes significant changes in $^{18}$F-dopa storage between scans throughout the brain and has recently been shown to be a useful method for detecting changes in dopaminergic function (Brooks, D. J. et al., 1990(a); Rakshi, J. S. et al., 1999) and for following the progression of PD (Whone, A. L. et al., The REAL-PET study: Slower progression in early Parkinson's disease treated with ropinirole compared with L-dopa, *Neurology*, 58, A82-A83 (2002)). When the preoperative and 6 month Ki images were interrogated with SPM three regions demonstrated focal increases in $^{18}$F-dopa uptake—(i) right posterior dorsal putamen (+17.9%), (ii) left medial dorsal putamen (+25.3%) and (iii) right substantia nigra (+16%). The exact locations of the regions with increased $^{18}$F-dopa uptake were identified with SPM superimposed on a mean MRI template constructed from the individual T1 weighted MRIs of the 5 patients. The movement of patient 2 during the 12 month scan again made interpretation of this small sample very difficult. Despite this, the patients as a group continued to demonstrate a significant increase in $^{18}$F-dopa within the right substantia nigra region (+26%; paired t test; P<0.05 uncorrected at cluster level).

$^{18}$F-dopa PET: Region of Interest Analysis

Repeated measures analysis of variance (MANOVA) identified a significant difference in the $^{18}$F-dopa uptake constant (Ki) between the baseline scan and all post-operative scans in the posterior putamen (p<0.001). The increase was most marked at 24 months (60%, p<0.001). A post-hoc comparison of the post-operative Ki values using the Tukey-Kramer multiple comparisons test demonstrated significantly higher $^{18}$F-dopa uptake at 24 months than at 6, 12 and 18 months in the posterior putamen (p<0.001 for 6 months vs. 24 months, p<0.05 for 12 months vs. 24 months, p<0.01 for 18 months vs. 24 months). Limiting the region of interest to the volume of putamen surrounding the catheter tip produced similar results but with a greater percentage increase in $^{18}$F-dopa uptake (83% at 24 months). Repeated measures analysis of variance also identified a significant difference in $^{18}$F-dopa uptake in the whole putamen (p=0.0237), the post-hoc analysis however was only able to identify a significant increase between baseline and 24 months. We were unable to identify any significant change in $^{18}$F-dopa uptake in either the head of caudate or the anterior half of dorsal putamen over the course of this study.

$^{18}$F-dopa PET: SPM

Pre-op and 24 month post surgery images of $^{18}$F-dopa uptake constants (Ki maps) were interrogated with SPM99. Two regions showed significant increases in $^{18}$F-dopa uptake: the left posterior dorsal putamen (p<0.0001 cluster corrected, Z score 3.01) and right posterior dorsal putamen (p<0.0001 cluster corrected, Z score 3.74). The right posterior dorsal putamen was also identified as a region of increased $^{18}$F-dopa uptake, albeit at a lower level of significance, when the baseline images were compared with the 6, 12, and 18 month Ki maps. The left posterior dorsal putamen was identified by SPM99 as a region of significantly increased $^{18}$F-dopa uptake when the baseline scans were compared with the 6 and 18 month Ki maps. The early SPM comparisons, i.e. baseline vs. 6 months and baseline vs. 12 months, localised a third region of increased $^{18}$F-dopa uptake involving the right substantia nigra. SPM99 was unable to identify increased $^{18}$F-dopa uptake in the right substantia nigra at 18 or 24 months.

CONCLUSIONS

Applicants show for the first time that direct intraputaminal GDNF infusion in patients with PD is safe, can be tolerated for at least two years and appears to effectively treat PD in humans. Furthermore, Applicants show for the first time that direct intraputaminal GDNF infusion in patients leads to sustained increases in dopamine uptake in the putamen. Although L-dopa equivalents were maintained in 3 of the 5 patients throughout this study, there was a significant reduction in dyskinetic movements by over 60% while on medication, and no dyskinetic movements off medication which has also been reported following intracerebral infusion of GDNF in monkeys (Miyoshi, Y. et al., Glial cell line-derived neurotrophic factor-levodopa interactions and reduction of side effects in parkinsonian monkeys. *Ann. Neurol.*, 42: 208-214 (1997)). This result is in contrast to recent fetal transplant trials where some patients experience dyskinesias of unknown origin when off medication (Freed, C., et al., Transplantation of embryonic dopamine neurons for severe Parkinson's disease. *N. Engl. J. Med.*, 344:710-719 (2001); Hagell, P., Dyskinesias following neural transplantation in Parkinson's disease. *Nat. Neurosci.*, 5: 627-628 (2002)). This finding is of major significance and a surprising benefit for PD patients and suggests that GDNF may act to regulate dopamine production, release and metabolism within the striatum thus allowing for a more physiological processing of motor output. Thus, PD patients administered GDNF directly to the putamen experience a far better quality "on" time than ever reported previously.

The overall 57% reductions in "off" UPDRS scores after 24 months of treatment are surprisingly dramatic. The improvements were progressive, with the "off" period scores at 12 months tending closely towards the baseline best "on" period scores. A decline in most CAPIT timed tests adds further evidence substantiating an overall subjective improvement. The finding of significant reductions in the UPDRS scores in the "on" clinical phase to 52% of baseline is unprecedented. No such improvement in the "on" state following surgical treatment for PD or following transplantation of fetal dopamine neurons has previously been reported (The Deep-Brain Stimulation for Parkinson's Disease Study Group, *New England Journal Medicine*, 345:956-963 (2001); Lindvall, O. & Hagell, P., Clinical observations after neural transplantation in Parkinson's disease., *Prog. Brain Res.*, 127: 299-320 (2000)).

PD is also often associated with impaired olfaction assumed to be the result of Lewy bodies in the olfactory bulb and cortex (Quinn, N. P. et al., Olfactory threshold in Parkinson's disease. *J. Neurol. Neurosurg. Psychiatry*, 50: 88-89 (1987); Daniel, S. E. & Hawkes, C. H., Preliminary diagnosis of Parkinson's disease by olfactory bulb pathology, *Lancet*, 340, 186 (1992)). In fact, three patients had long-standing loss of sensation of smell and taste, as is often the case in PD. Surprisingly, three patients reported a return of sense of smell following r-metHuGDNF infusion. These symptoms greatly improved or resolved completely between 3 and 6 weeks of r-metHuGDNF infusion. However, with this recovery, abnormal sensations of taste were intermittently experienced, with "metallic" or "soapy" tastes being reported.

At the highest dose of r-metHuGDNF, three patients also reported recovery of normal sexual function, both in terms of interest and potency. This recovery subsided as the dose was reduced.

The patients' functional performance was improved with infusion, as demonstrated by significant improvements in the activities of daily living scores (UPDRS part II and PDQ-39 ADL dimension).

It was apparent from the neuropsychological data that there was no detrimental effect of GDNF infusion on cognition. The cognitive test results in fact provide evidence of an improvement in verbal anterograde memory function in some patients after 24 months of GDNF infusion. The finding of improved memory function at 24 months was not attributable to practice. The comparable control group of 18 PD patients did not show a significant improvement in memory function after an interval of 12 months and in fact demonstrated significant declines on a number of measures of verbal anterograde memory function. It is also unlikely that the observed improvement in memory function is attributable to statistical false positive error. Out of the 54 statistical tests conducted one would expect 5 significant results by chance alone (with p=0.1). At 24 months there were, however, nine significant changes observed, two in the negative direction and seven in the positive direction. Of the positive changes observed six were on measures of anterograde verbal memory function.

In addition to clinical improvements, the continuous infusion of r-methHuGDNF was associated with surprisingly dramatic increases in total putamen $^{18}$F-dopa uptake capacity. Previous studies have estimated the annual decline in putamen $^{18}$F-dopa uptake to be around 10% of the baseline value in PD patients (Morrish, P. K., et al., 1996; Wenning, G. K. et al., Short- and long-term survival and function of unilateral intrastriatal dopaminergic grafts in Parkinson's disease. *Ann. Neurol.*, 42: 95-107 (1997)). In contrast, we report a 23.5% increase in total putamen $^{18}$F-dopa uptake following a two year infusion of GDNF into the posterior putamen. The increase in total putaminal $^{18}$F-dopa uptake and storage was entirely due to increases in the posterior half of the putamen or, more specifically, the putamen adjacent to the catheter tip (60% and 83%, respectively (p<0.01)). In contrast, there was only a 6.8% increase in $^{18}$F-dopa uptake in the anterior half of the putamen (p=0.223). In addition, in the patient who received GDNF unilaterally, a decline in total putamen $^{18}$F-dopa uptake of 7% over the course of the 2 years of follow up was detected. Thus, it is quite clear from these studies that the diffusion of GDNF in concentrations sufficient to induce significant changes in dopamine terminal function is limited. These results conflict with several previous animal studies in which the unilateral administration of GDNF to a unilaterally MPTP lesioned rhesus monkey resulted in significant increases in dopamine metabolites and nigral cell numbers on the contralateral side (Grondin, et al., 2002; Gash, et al., 1996). The difference between the relatively limited spread of GDNF activity in this study and the more widespread effects of GDNF in previous studies is probably due to brain size. The rhesus monkey brain is 12-15 times smaller than the human brain. As a consequence, diffusion from one hemisphere to another involves a relatively modest distance particularly following intra-nigral administration. The limited diffusion observed in this study is consistent with one recent primate study in which aged rhesus monkeys received unilateral intra-striatal infusions of 22.5 μg of GDNF per 24 hours. This study reported a maximal diffusion distance of 11 mm from the catheter tip. The present study clearly indicates that chronic administration of GDNF to the brain must be localized precisely in order to achieve therapeutic effectiveness in humans.

Increased dopamine storage at the level of the substantia nigra suggest that either local nigral dopamine terminals or neuron cell bodies were also responding to the r-metHuGDNF delivered to putamen nerve terminals possibly via its retrograde transport while the early changes in sense of smell, and the overall reductions in UPDRS at 3 months suggests at least an initial pharmacological action of r-metHuGDNF within the putamen. This is likely, in part, to involve a direct stimulatory effect on dopamine release as shown in rodent models (Hoffman, A. F., et al., In vivo microdialysis studies on somatodendritic dopamine release in the rat substantia nigra: effects of unilateral 6-OHDA lesions and GDNF. *Exp. Neurol.*, 147:130-141 (1997)).

---

---

We claim:

1. A method of producing a sustained increase in dopamine uptake within one or both putamen in a human suffering from Parkinson's disease that comprises locally administering to one or both putamen of a human in need thereof via convection-enhanced infusion using at least one catheter implanted for localized and targeted delivery into the putamen a pharmaceutical composition comprising a pharmaceutically effective amount of a glial cell-line derived neurotrophic factor (GDNF) protein product and at least one pharmaceutically acceptable vehicle, excipient, or diluent, wherein said GDNF protein product is administered in an amount and over a time effective to produce a sustained increase in dopamine uptake in the one or both putamen, and wherein the diffusion of said GDNF protein product resulting from such administration is limited to the putamen.

2. The method of claim 1 wherein said GDNF protein product is recombinant-methionyl human glial cell line-derived neurotrophic factor (r-metHuGDNF).

3. The method of claim 2 wherein said vehicle, excipient, or diluent comprises sodium chloride and sodium citrate.

4. A method of producing a sustained increase in dopamine uptake within one or both putamen in a human suffering from Parkinson's disease that comprises:
   assessing dopaminergic function in one or both putamen of said human, pre-operatively;
   identifying at least one site of dopaminergic dysfunction within one or both putamen;
   locally administering to one or both putamen of a human in need thereof via convection-enhanced infusion using at least one catheter implanted for localized and targeted delivery into the putamen a pharmaceutical composition comprising a pharmaceutically effective amount of a glial cell-line derived neurotrophic factor (GDNF) protein product and at least one pharmaceutically acceptable vehicle, excipient, or diluent, wherein said GDNF protein product is administered in an amount and over a time effective to produce a sustained increase in dopamine uptake in the one or both putamen, and wherein the diffusion of said GDNF protein product resulting from such administration is limited to the putamen; and,
   optionally, assessing dopaminergic function at one or more sites post-operatively, at least once.

5. The method of claim 4 wherein said GDNF protein product is r-metHuGDNF.

6. The method of claim 5 wherein said vehicle, excipient, or diluent comprises sodium chloride and sodium citrate.

7. The method of any one of claims 4 through 6, wherein assessing dopaminergic function comprises assessing dopamine uptake or dopamine storage.

8. The method of claim 7, wherein said site of dopaminergic dysfunction is the postero-dorsal region of one or both putamen.

9. The method of claim 7 wherein said site of dopaminergic dysfunction is the central region of one or both putamen.

10. A method of producing a sustained increase in dopamine uptake within one or both putamen, thereby increasing the function of dopaminergic neurons in a human in need thereof that comprises locally administering to one or both putamen of a human in need thereof via convection-enhanced infusion using at least one catheter implanted for localized and targeted delivery into the putamen a pharmaceutical composition comprising a pharmaceutically effective amount of a glial cell-line derived neurotrophic factor (GDNF) protein product and at least one pharmaceutically acceptable vehicle, excipient, or diluent, wherein said GDNF protein product is administered in an amount and over a time effective to produce a sustained increase in dopamine uptake in the one or both putamen, and wherein the diffusion of said GDNF protein product resulting from such administration is limited to the putamen.

11. The method of claim 10 wherein said GDNF protein product is r-metHuGDNF.

12. The method of claim 11 wherein said vehicle, excipient, or diluent comprises sodium chloride and sodium citrate.

13. The method of claim 12, wherein said pharmaceutical composition is administered to the postero-dorsal region of one or both putamen.

14. The method of claim 12, wherein said pharmaceutical composition is administered to the central region of one or both putamen.

15. A method of increasing the uptake of dopamine by dopaminergic neurons in a human that comprises locally administering to one or both putamen of a human in need thereof via convection-enhanced infusion using at least one catheter implanted for localized and targeted delivery into the putamen a pharmaceutical composition comprising a pharmaceutically effective amount of a glial cell-line derived neurotrophic factor (GDNF) protein product and at least one pharmaceutically acceptable vehicle, excipient, or diluent, wherein diffusion of said GDNF protein product is limited to the putamen of said human.

16. The method of claim 15 wherein said GDNF protein product is r-metHuGDNF.

17. The method of claim 16 wherein said vehicle, excipient, or diluent comprises sodium chloride and sodium citrate.

18. The method of claim 17, wherein said pharmaceutical composition is administered to the postero-dorsal region of one or both putamen.

19. The method of claim 17, wherein said pharmaceutical composition is administered to the central region of one or both putamen.

20. A method of regenerating dopaminergic neurons in a human that comprises locally administering to one or both putamen of a human in need thereof via convection-enhanced infusion using at least one catheter implanted for localized and targeted delivery into the putamen a pharmaceutical composition comprising a pharmaceutically effective amount of a glial cell-line derived neurotrophic factor (GDNF) protein product and at least one pharmaceutically acceptable vehicle, excipient, or diluent, wherein diffusion of said GDNF protein product is limited to the putamen of said human.

21. The method of claim 20 wherein said GDNF protein product is r-metHuGDNF.

22. The method of claim 21 wherein said vehicle, excipient, or diluent comprises sodium chloride and sodium citrate.

23. The method of claim 22, wherein said pharmaceutical composition is administered to the postero-dorsal region of one or both putamen.

24. The method of claim 22, wherein said pharmaceutical composition is administered to the central region of one or both putamen.

25. A method of protecting dopaminergic neurons susceptible to degeneration in a human that comprises locally administering to one or both putamen of a human in need thereof via convection-enhanced infusion using at least one catheter implanted for localized and targeted delivery into the putamen a pharmaceutical composition comprising a pharmaceutically effective amount of a glial cell-line derived neurotrophic factor (GDNF) protein product and at least one pharmaceutically acceptable vehicle, excipient, or diluent, wherein diffusion of said GDNF protein product is limited to the putamen of said human.

26. The method of claim 25 wherein said GDNF protein product is r-metHuGDNF.

27. The method of claim 26 wherein said vehicle, excipient, or diluent comprises sodium chloride and sodium citrate.

28. The method of claim 27, wherein said pharmaceutical composition is administered to the postero-dorsal region of one or both putamen.

29. The method of claim 27, wherein said pharmaceutical composition is administered to the central region of one or both putamen.

30. A method of treating Parkinson's disease in a human that comprises locally administering to a region of one or both putamen of a human in need thereof via convection-enhanced infusion using at least one catheter a pharmaceutical composition comprising a pharmaceutically effective amount of a glial cell-line derived neurotrophic factor (GDNF) protein product and at least one pharmaceutically acceptable vehicle, excipient, or diluent, wherein diffusion of said GDNF protein product is limited to the putamen of said human.

31. The method of claim 30 wherein said GDNF protein product is r-metHuGDNF.

32. The method of claim 31 wherein said vehicle, excipient, or diluent comprises sodium chloride and sodium citrate.

33. The method of claim 32, wherein said pharmaceutical composition is administered to the postero-dorsal region of one or both putamen.

34. The method of claim 32, wherein said pharmaceutical composition is administered to the central region of one or both putamen.

35. A method of treating Parkinson's disease in a human that comprises locally administering to one or both putamen of a human in need thereof via convection-enhanced infusion using at least one catheter implanted for localized and targeted delivery into the putamen a pharmaceutical composition comprising a pharmaceutically effective amount of a glial cell-line derived neurotrophic factor (GDNF) protein product and at least one pharmaceutically acceptable vehicle, excipient, or diluent, wherein diffusion of said GDNF protein product is limited to the putamen of said human.

36. The method of claim 35 wherein said GDNF protein product is r-metHuGDNF.

37. The method of claim 36 wherein said vehicle, excipient, or diluent comprises sodium chloride and sodium citrate.

38. The method of claim 37, wherein said pharmaceutical composition is administered to the postero-dorsal region of one or both putamen.

39. The method of claim 37, wherein said pharmaceutical composition is administered to the central region of one or both putamen.

40. The method of claim 1, 4, 10, 15, 20, 25, 30, or 35 wherein the GDNF protein product is administered at a dosage from about 1 µg/putamen/day to about 100 µg/putamen/day.

41. A method of producing a sustained increase in dopamine uptake within one or both putamen in a human suffering from Parkinson's disease, said method consisting essentially of the step of locally administering to one or both putamen of a human in need thereof via convection-enhanced infusion using at least one catheter implanted for localized and targeted delivery into the putamen a pharmaceutical composition comprising a pharmaceutically effective amount of a glial cell-line derived neurotrophic factor (GDNF) protein product and at least one pharmaceutically acceptable vehicle, excipient, or diluent, wherein said GDNF protein product is administered in an amount and over a time effective to produce a sustained increase in dopamine uptake in the one or both putamen, and wherein the diffusion of said GDNF protein product resulting from such administration is limited to the putamen of said human.

42. A method of producing a sustained increase in dopamine uptake within one or both putamen in a human suffering from Parkinson's disease, said method consisting of the step of locally administering to one or both putamen of a human in need thereof via convection-enhanced infusion using at least one catheter implanted for localized and targeted delivery into the putamen a pharmaceutical composition comprising a pharmaceutically effective amount of a glial cell-line derived neurotrophic factor (GDNF) protein product and at least one pharmaceutically acceptable vehicle, excipient, or diluent, wherein said GDNF protein product is administered in an amount and over a time effective to produce a sustained increase in dopamine uptake in the one or both putamen, and wherein the tissue distribution of said GDNF protein product resulting from such administration is limited to the putamen of said human.

43. The method according to any one of claims 1, 4, 10, 15, 20, 25, 30, 35, 41 and 42, wherein the administration of said pharmaceutical composition is pulsed.

* * * * *

SEQUENCE LISTING

```
<160> NUMBER OF SEQ ID NOS: 1

<210> SEQ ID NO 1
<211> LENGTH: 135
<212> TYPE: PRT
<213> ORGANISM: E. coli

<400> SEQUENCE: 1

Met Ser Pro Asp Lys Gln Met Ala Val Leu Pro Arg Arg Glu Arg Asn
 1               5                  10                  15

Arg Gln Ala Ala Ala Ala Asn Pro Glu Asn Ser Arg Gly Lys Gly Arg
            20                  25                  30

Arg Gly Gln Arg Gly Lys Asn Arg Gly Cys Val Leu Thr Ala Ile His
        35                  40                  45

Leu Asn Val Thr Asp Leu Gly Leu Gly Tyr Glu Thr Lys Glu Glu Leu
    50                  55                  60

Ile Phe Arg Tyr Cys Ser Gly Ser Cys Asp Ala Ala Glu Thr Thr Tyr
65                  70                  75                  80

Asp Lys Ile Leu Lys Asn Leu Ser Arg Asn Arg Arg Leu Val Ser Asp
                85                  90                  95

Lys Val Gly Gln Ala Cys Cys Arg Pro Ile Ala Phe Asp Asp Asp Leu
            100                 105                 110

Ser Phe Leu Asp Asp Asn Leu Val Tyr His Ile Leu Arg Lys His Ser
        115                 120                 125

Ala Lys Arg Cys Gly Cys Ile
    130                 135
```